(12) United States Patent
Kodama et al.

(10) Patent No.: US 6,472,525 B1
(45) Date of Patent: Oct. 29, 2002

(54) HEXAAZAISOWURTZITANE DERIVATIVE AND METHOD FOR PRODUCING THE SAME

(75) Inventors: Tamotsu Kodama, Fuji; Masahiro Tojo, Kurashiki; Masanori Ikeda, Fuji, all of (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 08/737,094

(22) Filed: May 16, 1997

Related U.S. Application Data

(63) Continuation-in-part of application No. PCT/JP96/00189, filed on Jan. 31, 1996.

(30) Foreign Application Priority Data

Feb. 1, 1995 (JP) ............................................. 7-014897

(51) Int. Cl.$^7$ ...................... C07D 259/00; C06B 25/34
(52) U.S. Cl. ...................... 540/554; 540/556; 149/92
(58) Field of Search ................ 540/554, 556; 149/92

(56) References Cited

U.S. PATENT DOCUMENTS

| | | | | |
|---|---|---|---|---|
| 5,693,794 A | * | 12/1997 | Nielson | 540/554 |
| 5,739,325 A | * | 4/1998 | Wardle et al. | 540/554 |
| 6,147,209 A | * | 11/2000 | Wardle et al. | 540/556 |
| 6,153,613 A | * | 11/2000 | Ono et al. | 514/252.13 |
| 6,153,749 A | * | 11/2000 | Kodama et al. | 540/556 |

FOREIGN PATENT DOCUMENTS

| | | | |
|---|---|---|---|
| EP | 753519 | * | 1/1997 |
| JP | 6-321962 | | 11/1994 |
| JP | 7-014897 | | 2/1995 |

OTHER PUBLICATIONS

Bellamy, A. J. "Reductive debenzylation of hexabenzyl-hexaazaisowurzitane," Tetrahedron vol. 51, (1995) pp. 4711–4722.*

Kodama et al. "Chemical Abstracts" 125:301030, 1996.*

Grant et al., Hackh's Chemical Dictionary, McGraw–Hill, Inc., pp. 14, 111, 114 and 412, 1987.*

Supplementary European Search Report EP 96 90 1500, Feb. 1997.

Department of Defense "The Militarily Critical Technologies List", pp. 12–19 to 12–25, Oct. 1992.

Nielsen et al. Polyazapolycyclics by Condensation of Aldehydes with Amines. 2. Formation of 2,4,6,8,10,12–Hexabenzyl–2,4,6,8,10,12–hexaazatetracyclo[5.5.0.0$^{5,9}$.0$^{3,11}$] dodecanes from Glyoxal and Benzylamines[1,2] J. Org. Chem., vol. 55, 1459–1466 (1990).

Oehrle, "Analysis of CL–20 and TNAZ in the Presence of Other Nitroaromatic and Nitramine Explosives Using HPLC with Photodiode Array PDA Detection", Journal of Energetic Materials, vol. 12, No. 4, 211–222, Dec. 1994.

\* cited by examiner

Primary Examiner—Brenda Coleman
(74) Attorney, Agent, or Firm—Finnegan, Henderson, Farabow, Garrett, & Dunner, L.L.P.

(57) ABSTRACT

Disclosed is an acyl group-containing hexaazaisowurtzitane derivative represented by the following formula (I): $W A_t Q_{(6-t)}$, wherein t represents an integer of from 4 to 6, A independently represents an acyl group having 1 to 10 carbon atoms, each Q independently represents a hydrogen atom or an alkyl group having 1 to 10 carbon atoms, and W represents a hexavalent hexaazaisowurtzitane residue represented by the following formula (II):

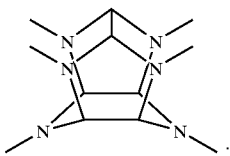

Also disclosed is a method for producing the above-mentioned acyl group-containing hexaazaisowurtzitane derivative. The acyl group-containing hexaazaisowurtzitane derivative of the present invention is useful as a precursor of a polynitrohexaazaisowurtzitane derivative which can be used not only as a material for explosives but also as an additive for propellants and explosives. The acyl group-containing hexaazaisowurtzitane derivative of the present invention is also useful as a raw material for producing a highly polar polymer, and as a polyfunctional crosslinking agent and an additive for polymers.

8 Claims, No Drawings

HEXAAZAISOWURTZITANE DERIVATIVE AND METHOD FOR PRODUCING THE SAME

This application is a continuation-in-part of PCT application No. PCT/JP96/Q0189, filed on Jan. 31, 1996, which designated the United States and on which priority is claimed under 35 U.S.C. §120.

BACKGROUND OF THE INVENTION

1. Field of The Invention

The present invention relates to an acyl group-containing hexaazaisowurtzitane derivative, and a method for producing the same.

The acyl group-containing hexaazaisowurtzitane derivative of the present invention contains an N—A group (wherein A represents an acyl group) and optionally an N—H group in high concentration, wherein each of the N—A group and the N—H group can be converted to an N—NO$_2$ group by various nitration methods.

Therefore, the acyl group-containing hexaazaisowurtzitane derivative of the present invention is useful as a precursor of a polynitrohexaazaisowurtzitane derivative which can be used not only as a material for explosives but also as an additive for propellants and explosives. More specifically, a polynitrohexaazaisowurtzitane derivative can be advantageously used as an additive for improving various properties (such as mechanical properties, detonation velocity, detonation pressure, burning rate, pressure exponent, sensitivity, and heat resistance) of propellants and explosives. In addition, hexanitrohexaazaisowurtzitane (hereinafter referred to simply as "HNW"), which is a typical example of the polynitrohexaazaisowurzitan derivative, has been expected to be a promising material for the next-generation high performance explosives. As mentioned above, the acyl group-containing hexaazaisowurtzitane derivative of the present invention is useful as a precursor of such a valuable polynitrohexaazaisowurtzitane derivative.

Further, the acyl group-containing hexaazaisowurtzitane derivative of the present invention can be advantageously used, by virtue of the reactivity of each of the N—A group (wherein A represents an acyl group) and the N—H group which are contained therein, for producing a highly polar polymer containing acyl groups in the main and/or side chain thereof in high concentration. This highly polar polymer is useful not only as a highly hydrophilic polymer but also as a highly dielectric polymer.

Still further, the acyl group-containing hexaazaisowurtzitane derivative of the present invention can be advantageously used as a polyfunctional crosslinking agent by virtue of the reactivity of the derivative.

Furthermore, the acyl group-containing hexaazaisowurtzitane derivative of the present invention can also be used as various types of additives, such as a polymer modifier and the like.

2. Prior Art

In addition to the above-mentioned HNW, conventionally known compounds, which have the same hexaazaisowurtzitane (hereinafter referred to simply as "W") skeleton as in the acyl group-containing hexaazaisowurtzitane derivative of the present invention, include the following:

(1) hexakis(arylmethyl)hexaazaisowurtzitane (hereinafter referred to simply as "HBW");
(2) tetraacetyldibenzylhexaazaisowurtzitane (hereinafter referred to simply as "TADBW"); and
(3) hexaazaisowurtzitane having a trimethylsilyl-ethyloxycarbonyl group (hereinafter referred to simply as "HCW") (see Unexamined Japanese Patent Application Laid-Open Specification No. 6-321962).

It is known that HBW can be obtained by a condensation reaction of various arylmethylamines with glyoxal [see J. Org. Chem., vol. 55, 1459–1466 (1990)].

It has been reported that TADBW is useful as a material for producing explosives [see The Militarily Critical Technologies List, Office of the Under Secretary of Defense for Acquisition, 12–22, October (1992)]. However, this reference neither describes a method for converting TADBW to an explosive, the chemical structure of such an explosive obtained from TADBW nor a method for producing TADBW itself.

The properties of HNW, which has been expected to be a promising material for high performance explosives as mentioned above, are described in International Symposium on Energetic Materials Technology, PROCEEDINGS, SEPTEMBER 24–27, 76–81 (1995); COMBUSTION AND FLAME 87, 145–151 (1991) and the like, but a method for producing HNW has not been reported in any literature.

Previously, with a view toward developing a method for producing a polynitrohexaazaisowurtzitane derivative, such as HNW, the present inventors tried to nitrate HBW and TADBW under various nitration conditions. However, it was impossible to obtain a satisfactory amount of a polynitrohexaazaisowurtzitane derivative. Further, HBW and TADBW have a benzyl group, so that, when HBW or TADBW is subjected to nitration, nitroaromatic compounds having high affinity for various nitro compounds are inevitably produced as a by-product. As a result, it is difficult to separate the desired polynitrohexaazaisowurtzitane derivative from the by-produced nitroaromatic compounds.

It is also difficult to obtain HCW in high yields. The reason for this is considered to reside in that, during the production of HCW, hydrochloric acid (which is a strong acid) is generated, and the generated hydrochloric acid is likely to decompose HBW as a starting material.

Thus, all of the W skeleton-containing compounds of HBW, TADBW and HCW are not suitable as precursors which can be advantageously used for producing a polynitrohexaazaisowurtzitane derivative, such as HNW or the like, on a commercial scale.

SUMMARY OF THE INVENTION

In these situations, with a view toward developing a commercially advantageous method for producing a polynitrohexaazaisowurtzitane derivative, the present inventors have made extensive and intensive studies in order to find not only a precursor which can be easily converted to a polynitrohexaazaisowurtzitane derivative, but also a method for producing the precursor.

As a result, it has unexpectedly been found that a hexaazaisowurtzitane derivative having a polar group moiety comprised only of an N-acyl group and optionally an N—H group is useful as a precursor of a polynitrohexaazaisowurtzitane derivative. The present inventors have also found a commercially advantageous method for producing the above-mentioned hexaazaisowurtzitane derivative in high yield. It has further been found that a hexaazaisowurtzitane derivative having an N-acyl group, an N-alkyl group and optionally an N—H group can be advantageously used as a polyfunctional crosslinking agent. The present invention has been completed based on these novel findings.

It is an object of the present invention to provide the above-mentioned hexaazaisowurtzitane derivative, and it is another object of the present invention to provide a method for producing the same.

It is a further object of the present invention to provide a novel functional material which contains a highly polar, functional group, such as an N—acyl group and an N—H group, in high concentration.

DETAILED DESCRIPTION OF THE INVENTION

In one aspect of the present invention, there is provided an acyl group-containing hexaazaisowurtzitane derivative represented by the following formula (I):

$WA_tQ_{(6-t)}$ (I)

wherein t represents an integer of from 4 to 6, each A independently represents an acyl group having 1 to 10 carbon atoms, each Q independently represents a hydrogen atom or an alkyl group having 1 to 10 carbon atoms, and W represents a hexavalent hexaazaisowurtzitane residue represented by the following formula (II):

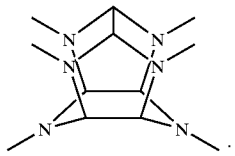

(II)

In another aspect of the present invention, there is provided a method for producing the above-mentioned acyl group-containing hexaazaisowurtzitane derivative.

Hereinbelow, explanation is made with respect to an acyl group-containing hexaazaisowurtzitane derivative represented by formula (I-a) below, as a typical example of the compound of formula (I) above.

$WA_tH_{(6-t)}$ (I-a)

wherein t represents an integer of from 4 to 6, A represents an acyl group having 1 to 10 carbon atoms, H represents a hydrogen atom, and W represents a hexavalent hexaazaisowurtzitane residue represented by the following formula (II):

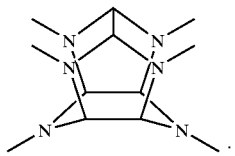

(II)

With respect to the acyl group A in the hexaazaisowurtzitane derivative of the present invention, there is no particular limitation as long as it has 1 to 10 carbon atoms. The acyl group may be substituted with a substituent which is stable under reaction conditions for a reductive dearylmethylation reaction conducted in the method of the present invention as described below. Examples of acyl groups include an acetyl group, a propionyl group, a butyryl group, an isobutyryl group, a valeryl group, a hexanoyl group and a 2-phenylacetyl group. Of these, acyl groups having 2 to 5 carbon atoms, such as an acetyl group, a propionyl group, a butyryl group and a valeryl group, are preferred. Acyl groups having 2 to 3 carbon atoms, such as an acetyl group and a propionyl group, are more preferred. The acyl groups represented by $A_t$ in formula (I-a) above may be the same or different.

With respect to the acyl group-containing hexaazaisowurtzitane derivative of the present invention represented by formula (I-a): $WA_tH_{(6-t)}$, a plurality of types of isomers are present which have the same value for t but are different in regard to the positions of N-acyl groups and N—H groups.

For example, as a representative example of compounds represented by formula (I-a) $WA_tH_{(6-t)}$ wherein t is 4, i.e., compounds represented by the formula $WA_4H_2$, a compound represented by the formula (I-a') below can be mentioned, but the compound represented by formula $WA_4H_2$ may be any of the structural isomers of the compound of formula (I-a') below:

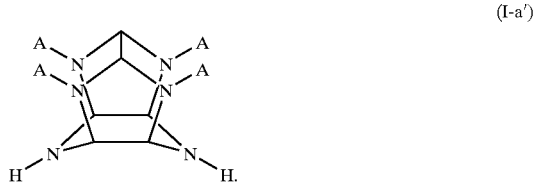

(I-a')

In the acyl group-containing hexaazaisowurtzitane derivative $WA_tH_{(6-t)}$ of the present invention, t represents an integer of from 4 to 6, preferably 4 or 6.

One preferred example of the acyl group-containing hexaazaisowurtzitane derivative of the present invention is a compound represented by formula (I-a) wherein t is 6, that is, a hexaacylhexaazaisowurtzitane represented by the following formula (III):

$WA_6$ (III)

wherein A represents an acyl group having 1 to 10 carbon atoms, and W represents a hexavalent hexaazaisowurtzitane residue.

The hexaacylhexaazaisowurtzitane of formula (III) above is advantageous in that, since the structure of the compound is simple, the compound can be easily obtained in a highly purified form. In this connection, it should further be noted that, among compounds of formula (III), a hexaacetyl compound can be purified by sublimation, so that a highly purified $WA_6$ (A: acetyl group) can be easily obtained from a reaction mixture.

Another preferred example of an acyl group-containing hexaazaisowurtzitane derivative of the present invention is a compound represented by formula (I-a) wherein t is 4. This compound is advantageous in that since N—H groups contained therein have high reactivity, it is possible for the N—H groups to be selectively reacted. For example, by selectively nitrating the N—H groups, a dinitrohexaazaisowurtzitane derivative can be easily obtained in high yield.

As mentioned above, the acyl group-containing hexaazaisowurtzitane derivative of the present invention contains an N—A group (wherein A represents an acyl group) and optionally an N—H group in high concentration, wherein each of the N—A group and the N—H group can be converted to an N—NO$_2$ group by various nitration methods.

The following examples describe methods for producing the acyl group-containing hexaazaisowurtzitane derivative of formula (I-a).

The hexaacylhexaazaisowurtzitane $WA_6$, which is a preferred example of the acyl group-containing hexaazaisowurtzitane derivative of the present invention, can be obtained by acylating the acyl group-containing hexaazaisowurtzitane derivative $WA_nH_{(6-n)}$ (wherein n is 4 or 5) with an acylating agent as shown in the following formula (1):

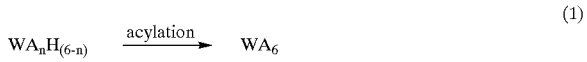

(1)

wherein n represents an integer of from 4 to 5, A represents an acyl group having 1 to 10 carbon atoms, H represents a hydrogen atom, and W represents a hexavalent hexaazaisowurtzitane residue.

The $WA_nH_{(6-n)}$ (wherein n is 4 or 5) used in the reaction of formula (1) above is not disclosed in any prior art literature, and has for the first time been synthesized by the present inventors. The method for producing the $WA_nH_{(6-n)}$ first requires the following explanation of the method for producing $WA_6$.

With respect to the acylating agent used in the reaction of formula (1), there is no particular limitation as long as it is capable of acylating a secondary amino group contained in the $WA_nH_{(6-n)}$ (wherein n is 4 or 5). Examples of acylating agents include acyl halides, such as acetyl chloride, acetyl bromide and propionyl chloride; carboxylic esters of N-hydroxysuccinimide, such as N-acetoxysuccinimide, N-propionyloxysuccinimide and N-(2-phenylacetoxy)succinimide; carboxylic anhydrides, such as acetic anhydride, propionic anhydride, lactic anhydride and an anhydride of a mixture of acetic and formic acid; and acylimidazoles, such as acetylimidazole and propionylimidazole. Among the above-mentioned acylating agents, acyl halides (such as acetyl chloride, propionyl chloride and the like) are preferred.

With respect to a reaction solvent to be used in the reaction of formula (1), there is no particular limitation as long as the solvent is capable of dissolving the $WA_nH_{(6-n)}$ (wherein n is 4 or 5) and the solvent does not adversely affect the reaction. Examples of solvents include carboxylic acids, such as acetic acid, propionic acid and lactic acid; aprotic polar solvents, such as dimethyl sulfoxide and dimethylacetamide; and carboxylic anhydrides, such as acetic anhydride and propionic anhydride. Of these, carboxylic anhydrides (such as acetic anhydride, propionic anhydride and the like) are preferred. The above-mentioned solvents can be used individually or in combination.

The reaction temperature for the reaction of formula (1) is generally in the range of from −10 to 300° C., preferably from 0 to 150° C.

The $WA_6$ obtained by the reaction of formula (1) can be isolated by a conventional method. For example, the isolation of the $WA_6$ can be conducted by distilling off the solvent from the reaction mixture after completion of the reaction (see, for example, Example 1). Also, the purification of the $WA_6$ can be conducted by a conventional method. Examples of methods for the purification include a method in which the isolated $WA_6$ is subjected to sublimation at 270° C. under reduced pressure of 10 mmHg (see, for example, Example 1); a method in which the isolated $WA_6$ is recrystallized from toluene (see, for example, Example 2); and a method in which the isolated $WA_6$ is reprecipitated from chloroform.

The $WA_6$ of the present invention can also be obtained by subjecting an acyl group- and arylmethyl group-containing hexaazaisowurtzitane derivative represented by the formula $WA_nB_{(6-n)}$ to reductive dearylmethylation and then, acylating the resultant with an acylating agent, as shown in the following formula (2):

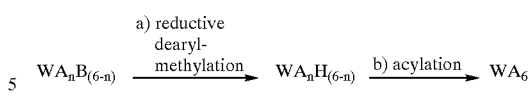

(2)

wherein n represents an integer of from 4 to 5; A represents an acyl group having 1 to 10 carbon atoms; B represents an arylmethyl group represented by formula (XIII) described below; H represents a hydrogen atom; and W represents a hexavalent hexaazaisowurtzitane residue.

The $WA_nB_{(6-n)}$ as the starting material in the reaction of formula (2) above has no particular limitation on the source or method of production thereof.

For example, $WA_nB_{(6-n)}$ which is produced from a hexakis(arylmethyl)hexaazaisowurtzitane $(WB_6)$ by a method as described below or which is commercially available can be used without any restriction.

In the above-mentioned process of formula (2), the reductive dearylmethylation (step a) can be performed according to any of conventional methods, as long as it is capable of advancing the reductive dearylmethylation reaction of the $WA_nB_{(6-n)}$. Generally, the reductive dearylmethylation (step a) is performed by contacting the $WA_nB_{(6-n)}$ with a reduction catalyst in the presence of a reducing agent.

As the reducing agent, hydrogen gas, hydrazine, formic acid or the like is generally used, and hydrogen gas is preferably used. As the reduction catalyst, a catalyst containing a metal belonging to the platinum family or containing a derivative thereof, is generally used. Preferred examples of reduction catalysts include Pd compounds [such as $Pd(OAc)_2$, $PdCl_2$, $Pd(NO_3)_2$, PdO, $Pd(OH)_2$, $Pd_3Pb_1$ and $Pd_3Te_1$], Pd alloys and metallic Pd; and Ru compounds (such as $RuCl_3$), Ru alloys and metallic Ru. Of these, Pd compounds [such as $Pd(OAc)_2$, $PdCl_2$ and the like], Pd alloys and metallic Pd are more preferred. These reduction catalysts as such can be used. Alternatively, these reduction catalysts can be used in such a form as carried on various types of carriers, such as activated carbon, silica, alumina, silica-alumina, zeolite and activated clay. The catalyst may be subjected to reduction treatment prior to use in the above-mentioned reductive dearylmethylation reaction. In the case of a catalyst carried on a carrier, the acidity of the surface of the carrier can be controlled by inactivating acid sites present on the surface of the carrier by silylation, acylation or the like, or treating the carrier so that an alkaline substance (e.g., NaOH) is adsorbed on the surface of the carrier. The amount of the reduction catalyst varies depending on the reducing activity of the catalyst. However, the catalyst is used generally in an amount of from 0.0001 to 10, preferably from 0.001 to 1, in terms of the weight ratio of the metal of the catalyst to the $WA_nB_{(6-n)}$.

With respect to a reaction solvent to be used in the reductive dearylmethylation (step a) of the process of formula (2) above, there is no particular limitation as long as the solvent is capable of dissolving the $WA_nB_{(6-n)}$ and the solvent does not adversely affect the reaction. Examples of solvents include carboxylic acids, such as acetic acid, propionic acid and lactic acid; amide compounds, such as dimethylacetoamide; and amine compounds, such as N,N-dimethylaniline. The above-mentioned solvents can be used individually or in combination. From the viewpoint of achieving a high reaction rate, it is preferred to use a carboxyilic acid (such as acetic acid, propionic acid or the like) as the solvent.

The amount of the solvent varies depending on the dissolving capability of the solvent and the reaction temperature. The solvent is used generally in an amount of from 1 to 500, preferably from 5 to 100, in terms of the weight ratio of the solvent to the $WA_nB_{(6-n)}$.

The reaction pressure for the reductive dearylmethylation (step a) of the process of formula (2) is generally in the range of from 0.1 to 1,000 kgf/cm$^2$, preferably from 1 to 100 kgf/cm$^2$. When hydrogen gas is used as a reducing agent, the reaction pressure is preferably in the range of from 0.1 to 500 kgf/cm$^2$, more preferably from 1 to 100 kgf/cm$^2$, in terms of hydrogen partial pressure. In addition to the hydrogen gas, inert gases, such as nitrogen, argon and helium gases, may be present in the reaction system.

The reaction temperature for the reductive dearylmethylation (step a) of the process of formula (2) is generally in the range of from −20 to 300° C., preferably from 0 to 200° C.

The reaction time for the reductive dearylmethylation (step a) of the process of formula (2) varies depending on the types of the catalyst, solvent, and the like. The reaction time is generally in the range of from 0.1 to 500 hours, preferably from 1 to 200 hours.

By the reductive dearylmethylation reaction (step a) of the process of formula (2), a $WA_nH_{(6-n)}$ (wherein n is 4 or 5) is synthesized. Then, the synthesized $WA_nH_{(6-n)}$ is subjected to acylation (step b) of the process of formula (2).

With respect to the acylating agent, solvent and reaction conditions (such as reaction temperature and the like) employed in the acylation (step b) of the process of formula (2), those which are mentioned in connection with the acylation reaction of formula (1) above can be employed.

The isolation and the purification of the obtained $WA_6$ can be conducted by the method mentioned in connection with the reaction of formula (1) above.

The $WA_6$ which is one example of the acyl group-containing hexaazaisowurtzitane derivative of the present invention can also be obtained by subjecting $WB_6$ to reductive dearylmethylation in the presence of an acylating agent to obtain a first reaction product and then, subjecting the first reaction product to reductive dearylmethylation in the absence of an acylating agent to obtain a second reaction product and then subjecting the second reaction product to acylation, as shown in the following formula (3):

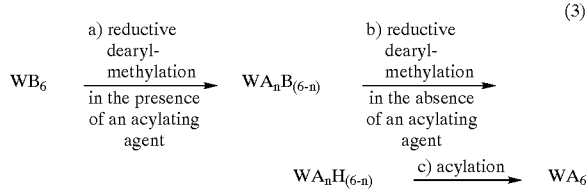

(3)

wherein n represents an integer of from 4 to 5; A represents an acyl group having 1 to 10 carbon atoms; B represents an arylmethyl group; and W represents a hexavalent hexaazaisowurtzitane residue.

The reductive dearylmethylation in the presence of an acylating agent in step a of the process of formula (3) above is generally performed by contacting $WB_6$ with a reduction catalyst in the presence of an acylating agent and a reducing agent. With respect to the reducing agent and the catalyst, there is no particular limitation as long as they can advance the reductive dearylmethylation reaction of the $WB_6$ and do not deactivate the acylating agent in the reaction system. As the reducing agent, hydrogen gas, formic acid or the like is generally used, and hydrogen gas is preferably used. As the reduction catalyst, those which are mentioned in connection with the reductive dearylmethylation (step a) of the process of formula (2) above can be employed.

The amount of the catalyst varies depending on the reducing activity of the catalyst. The reduction catalyst is used generally in an amount of from 0.0001 to 20, preferably from 0.001 to 10, in terms of the weight ratio of the metal of the catalyst to the $WB_6$.

With respect to the acylating agent to be used in the reductive dearylmethylation in the presence of an acylating agent in step a of the process of formula (3), there is no particular limitation as long as it is capable of acylating a secondary amino group which is formed by the reductive dearylmethylation of the $WB_6$. Examples of acylating agents include carboxylic esters of N-hydroxysuccinimide, such as N-acetoxysuccinimide, N-propionyloxysuccinimide and N-(2-phenylacetoxy)succinimide; carboxylic anhydrides, such as acetic anhydride, propionic anhydride, lactic anhydride and an anhydride of a mixture of acetic and formic acid; and acylimidazoles, such as acetylimidazole and propionylimidazole. Among these acylating agents, carboxylic esters of N-hydroxysuccinimide (such as N-acetoxysuccinimide, N-propionyloxysuccinimide and the like) are preferred because the selectivity for a $WA_nB_{(6-n)}$ (wherein n is 4 or 5) is improved. These acylating agents can be used individually or in combination. Especially, a mixture of a carboxylic ester of N-hydroxysuccinimide (such as N-acetoxysuccinimide, N-propionyloxysuccinimide or the like) and a carboxylic anhydride (such as acetic anhydride, propionic anhydride or the like) is preferred as the acylating agent, because not only does the reaction rate of the reductive dearylmethylation in step a of the process of formula (3) become high, but the selectivity for a $WA_nB_{(6-n)}$ (wherein n is 4 or 5) is also improved.

The amount of the acylating agent varies depending on the reactivity of the acylating agent, the reaction mode and the reaction conditions. The acylating agent is used generally in an amount of from 0.1 to 100, preferably from 1 to 50, in terms of the molar ratio of the acylating agent to the arylmethyl groups of the $WB_6$. When the mixture of a carboxylic ester of N-hydroxysuccinimide and a carboxylic anhydride is used as the acylating agent, the amount of the carboxylic anhydride is generally in the range of from 0.01 to 100, preferably from 0.1 to 10, in terms of the molar ratio of the carboxylic anhydride to the carboxylic ester of N-hydroxysuccinimide.

With respect to a reaction solvent to be used in the reductive dearylmethylation in the presence of an acylating agent in step a of the process of formula (3), there is no particular limitation as long as the solvent is capable of dissolving the $WB_6$ and the solvent does not adversely affect the reaction. Examples of solvents include aromatic compounds, such as benzene, toluene, ethylbenzene, xylene, cumene, cymene, diisopropylbenzene and phenyl ethyl ether; cyclic, linear or branched ethers, such as tetrahydrofuran, dioxane, tetrahydropyran, diethyl ether, dipropyl ether and diisopropyl ether; and aliphatic alcohols, such as methanol, ethanol, propanol, isopropyl alcohol and t-butyl alcohol. These solvents can be used individually or in combination. Among the above-mentioned solvents, aromatic compounds (such as benzene, toluene, ethylbenzene, xylene and the like) are preferred because the reaction rate of the reductive dearylmethylation reaction of the $WB_6$ increases with these solvents.

The amount of the solvent varies depending on the dissolving capability of the solvent and the reaction temperature. The solvent is used generally in an amount of from 0.1 to 100, preferably from 1 to 100, in terms of the weight ratio of the solvent to the $WB_6$.

The reaction pressure for the reductive dearylmethylation (in the presence of an acylating agent) in step a of the process of formula (3) is generally in the range of from 0.1 to 1,000 kgf/cm$^2$, preferably from 1 to 300 kgf/cm$^2$. When hydrogen gas is used as the reducing agent, in some cases, the reaction rate is increased in accordance with the increase of the reaction pressure. The reaction pressure is preferably in the range of from 0.1 to 500 kgf/cm$^2$, more preferably from 1 to 200 kgf/cm$^2$, in terms of the hydrogen partial pressure. In addition to the hydrogen gas, inert gases, such as nitrogen, argon and helium gases, may be present in the reaction system.

The reaction temperature for the reductive dearylmethylation (in the presence of an acylating agent) in step a of the process of formula (3) is generally in the range of from −20 to 300° C., preferably from 0 to 200° C.

In the process of formula (3), the reductive dearylmethylation reaction (step a) is terminated when the $WA_nB_{(6-n)}$ has been formed in a substantial amount. Specifically, the advance of the dearylmethylation reaction is monitored by gas chromatography or liquid chromatography, and the reaction is terminated when the $WA_nB_{(6-n)}$ has been formed in a desired amount.

The reaction time varies depending on the types of the catalyst, acylating agent, solvent, and the like. The reaction time is generally in the range of from 0.1 to 500 hours, preferably from 1 to 200 hours.

By the reductive dearylmethylation (in the presence of an acylating agent) in step a of the process of formula (3), a $WA_nB_{(6-n)}$ (wherein n is 4 or 5) is synthesized. Then, the synthesized $WA_nB_{(6-n)}$ is subjected to reductive dearylmethylation (in the absence of an acylating agent) in step b of the process of formula (3).

With respect to the catalyst, reducing agent, solvent, and reaction conditions (reaction temperature, reaction pressure, and the like) to be employed in the reductive dearylmethylation (in the absence of an acylating agent) in step b of the process of formula (3), those which are mentioned in connection with the reductive dearylmethylation (in the presence of an acylating agent) in step a of the process of formula (3) above can be employed. Alternatively, the catalyst, reducing agent, solvent and reaction conditons which are mentioned in connection with the reductive dearylmethylation in step a of the process of formula (2) above can be employed.

From the reaction mixture obtained by the reductive dearylmethylation (in the presence of an acylating agent) in step a of the process of formula (3), the acylating agent is removed, and the resultant acylating agent-removed mixture is subjected to reductive dearylmethylation (in the absence of an acylating agent) in step b of the process of formula (3). In this instance, it is preferred not to remove the reduction catalyst and solvent used in the reductive dearylmethylation in step a, but to leave it in the reaction mixture obtained by the reductive dearylmethylation in step a and use it in situ in the next reductive dearylmethylation in step b.

Reductive dearylmethylation (in the absence of an acylating agent) in step b of the process of formula (3) synthesizes a $WA_nH_{(6-n)}$ (wherein n is 4 or 5) which is then subjected to acylation in step c of the process of formula (3).

With respect to the acylating agent, solvent and reaction conditions (reaction temperature, and the like) to be employed in the acylation in step c of the process of formula (3), those which are mentioned in connection with the acylation reaction of formula (1) above can be employed.

The reaction mixture obtained by the reductive dearylmethylation (in the absence of an acylating agent) in step b of the process of formula (3) above can be subjected to in situ acylation with an acylating agent in step c of the process of formula (3). Alternatively, the reaction mixture obtained by the reductive dearylmethylation in step b can be subjected to acylation in step c after the reduction catalyst and/or the solvent has been removed from the reaction mixture.

The isolation and the purification of the obtained $WA_6$ can be conducted by the method mentioned in connection with the reaction of formula (1) above.

The $WA_6$ can also be obtained by subjecting a $WA_nB_{(6-n)}$ to reductive dearylmethylation in the presence of an acylating agent, as shown by the following formula (4):

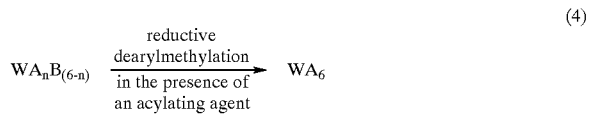

(4)

wherein n represents an integer of from 4 to 5, A represents an acyl group having 1 to 10 carbon atoms, B represents an arylmethyl group, and W represents a hexavalent hexaazaisowurtzitane residue.

With respect to the reducing agent, reduction catalyst, acylating agent, solvent, reaction conditions (e.g., reaction temperature, reaction pressure, and the like), those which are mentioned in connection with the reaction of formula (9) (infra) can be used.

The $WA_6$ can also be obtained by subjecting a $WB_6$ to reductive dearylmethylation in the presence of an acylating agent, as shown by the following formula (5):

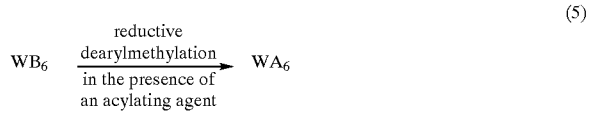

(5)

wherein B represents an arylmethyl group, A represents an acyl group having 1 to 10 carbon atoms, and W represents a hexavalent hexaazaisowurtzitane residue.

With respect to the reducing agent, reduction catalyst, acylating agent, solvent, reaction conditions and the like to be employed in the reaction of formula (5) above, those which are mentioned in connection with step a of the process of formula (3) above can be employed.

The isolation and the purification of the obtained $WA_6$ can be conducted by the method mentioned in connection with the reaction of formula (1) above.

As another example of the acyl group-containing hexaazaisowurtzitane derivative of the present invention, a compound represented by the formula $WA_nH_{(6-n)}$ (wherein n is 4 or 5) can be mentioned, which can be obtained by subjecting a $WA_nB_{(6-n)}$ (wherein n is 4 or 5) to reductive dearylmethylation in the absence of an acylating agent, as shown in the following formula (6):

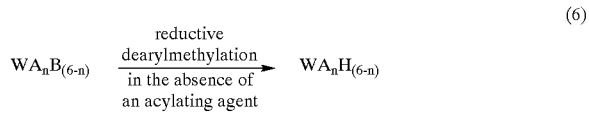

(6)

wherein n represents an integer of from 4 to 5, A represents an acyl group having 1 to 10 carbon atoms, B represents an arylmethyl group, and W represents a hexavalent hexaazaisowurtzitane residue.

With respect to the reducing agent, reduction catalyst, solvent, reaction conditions and the like to be employed in the reaction of formula (6) above, those which are mentioned in connection with step a of the process of formula (2) above can be employed.

The $WA_nH_{(6-n)}$ obtained by the reaction of formula (6) can be isolated by a conventional method. For example, the isolation can be conducted by a method comprising: removing the catalyst by filtration from the reaction mixture after completion of the reductive dearylmethylation reaction, thereby obtaining a filtrate; and distilling off the solvent from the obtained filtrate (see, for example, Example 5).

The acyl group-containing hexaazaisowurtzitane derivative $WA_nH_{(6-n)}$ (wherein n is 4 or 5) of the present invention can also be obtained by a) subjecting $WB_6$ to reductive dearylmethylation in the presence of an acylating agent and then, b) subjecting the resultant to reductive dearylmethylation in the absence of an acylating agent, as shown in the following formula (7):

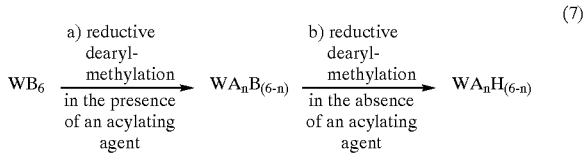
(7)

wherein n represents an integer of from 4 to 5, A represents an acyl group having 1 to 10 carbon atoms, B represents an arylmethyl group, H represents a hydrogen atom, and W represents a hexavalent hexaazaisowurtzitane residue.

With respect to the reducing agent, reduction catalyst, acylating agent, solvent, reaction conditions and the like to be employed in the reductive dearylmethylation (in the presence of an acylating agent) in step a of the process of formula (7) above, those which are mentioned in connection with step a of the process of formula (3) above can be employed.

By the reductive dearylmethylation (in the presence of an acylating agent) in step a of the process of formula (7), a $WA_nB_{(6-n)}$ (wherein n is 4 or 5) is synthesized, and the synthesized $WA_nB_{(6-n)}$ is subjected to reductive dearylmethylation (in the absence of an acylating agent) in step b of the process of formula (7).

With respect to the reducing agent, reduction catalyst, solvent, reaction conditions and the like to be employed in the reductive dearylmethylation (in the absence of an acylating agent) in step b of the process of formula (7), those which are mentioned in connection with step b of the process of formula (3) above can be used.

The isolation of the obtained $WA_nH_{(6-n)}$ can be conducted by the method mentioned in connection with the reaction of formula (6) above.

The $WA_nB_{(6-n)}$, which is a starting material for synthesizing the acyl group-containing hexaazaisowurtzitane derivative $WA_nH_{(6-n)}$ of the present invention, can be obtained by subjecting a $WB_6$ to reductive dearylmethylation in the presence of an acylating agent, as shown in the following formula (8):

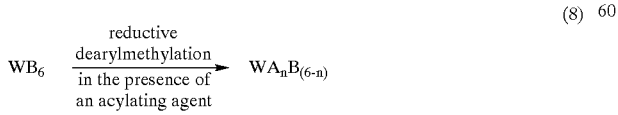
(8)

wherein n represents an integer of from 4 to 5, A represents an acyl group having 1 to 10 carbon atoms, B represents an arylmethyl group, and W represents a hexavalent hexaazaisowurtzitane residue.

With respect to the reducing agent, reduction catalyst, acylating agent, solvent, reaction conditions and the like to be employed in the reaction of formula (8) above, those which are mentioned in connection with step a of the process of formula (3) above can be employed.

The $WA_nB_{(n-6)}$ obtained by the reaction of formula (8) can be isolated by a conventional method. For example, the isolation can be conducted by a method comprising: subjecting the reaction mixture obtained by the reductive dearylmethylation to filtration using a filter paper to filter off a precipitate and the catalyst; treating the precipitate on the filter paper with chloroform to dissolve the precipitate therein; distilling off the solvent and chloroform from the filtrate to obtain a solid residue; dissolving the solid residue in chloroform to obtain a solution; adding an aqueous ammonia solution to the obtained solution; separating the resultant mixture into an aqueous phase and a chloroform phase; isolating the chloroform phase; and distilling off the solvent from the chloroform phase (see, for example, Example 19).

In the above-mentioned reductive dearylmethylation reaction in the presence of an acylating agent, a side reaction occurs in which an N-acyl group formed by the main reaction is further reduced to an N-alkyl group.

Thus, as mentioned above, according to the present invention, there is also provided an N-alkyl group-containing hexaazaisowurtzitane derivative represented by the following formula (XII):

$$WA_nQ_{(6-n)} \quad \text{(XII)}$$

wherein n represents an integer of from 4 to 5, each A independently represents an acyl group having 1 to 10 carbon atoms, each Q independently represents a hydrogen atom or an alkyl group having 1 to 10 carbon atoms provided that all of Q's are not simultaneously hydrogen atoms, and W represents a hexavalent hexaazaisowurtzitane residue represented by the following formula (II):

(II)

As mentioned above, the N-alkyl group-containing hexaazaisowurtzitane derivative can be advantageously used as a polyfunctional crosslinking agent.

Examples of N-alkyl group-containing hexaazaisowurtzitanes include diethyltetraacetylhexaazaisowurtzitane ($WA_4R_2$) obtained in Examples 6–12, ethylpentaacetylhexaazaisowurtzitane ($WA_5R_1$) obtained in Examples 13 and 14, and monoalkyltetraacetylhexaazaisowurtzitane ($WA_4RH$) shown in Chart [formula (12)].

The N-alkyl group-containing hexaazaisowurtzitane derivative can be obtained by subjecting a $WA_nB_{(6-n)}$ to reductive dearylmethylation in the presence of an acylating agent, as shown in the following formula (9):

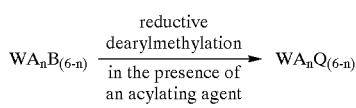

(9)

wherein n represents an integer of from 4 to 5, A represents an acyl group having 1 to 10 carbon atoms, B represents an arylmethyl group, each Q independently represents a hydrogen atom or an alkyl group having 1 to 10 carbon atoms provided that all of Q's are not simultaneously hydrogen atoms, and W represents a hexavalent hexaazaisowurtzitane residue.

The reductive dearylmethylation reaction of formula (9) above can be effected under substantially the same conditions as mentioned in connection with the reductive dearylmethylation reaction in step a of the process of formula (2) above, except that the reaction of formula (9) is conducted in the presence of an acylating agent.

In the reductive dearylmethylation reaction (in the presence of an acylating agent) of formula (9), the acylating agents which are mentioned in connection with step a of the process of formula (3) above can be used in substantially the same manner as described in that step.

With respect to the solvent, reduction catalyst, acylating agent, reaction conditions (e.g., reaction temperature and reaction pressure) and the like to be employed in the reaction of formula (9), those which are mentioned in connection with step a of the process of formula (3) above can also be employed.

The $WA_nQ_{(6-n)}$ obtained by the reaction of formula (9) can be isolated by a conventional method. For example, the isolation can be conducted by a method comprising: removing the catalyst from the reaction mixture by filtration to obtain a filtrate; and distilling off the solvent from the filtrate (see, for example, Example 6).

The $WA_nQ_{(6-n)}$ can also be obtained by subjecting a $WB_6$ to reductive dearylmethylation in the presence of an acylating agent, as shown in the following formula (10):

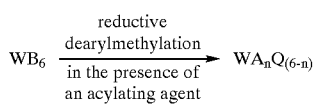

(10)

wherein n represents an integer of from 4 to 5, A represents an acyl group having 1 to 10 carbon atoms, B represents an arylmethyl group, each Q independently represents a hydrogen atom or an alkyl group having 1 to 10 carbon atoms provided that all of Q's are not simultaneoulsy hydrogen atoms, and W represents a hexavalent hexaazaisowurtzitane residue.

With respect to the solvent, reduction catalyst, acylating agent, reaction conditions and the like to be employed in the reaction of formula (10), those which are mentioned in connection with step a of the process of formula (3) above can be employed.

The isolation of the obtained $WA_nQ_{(6-n)}$ can be conducted by the method mentioned in connection with the reaction of formula (9) above.

In the $WB_6$ and $WA_nB_{(6-n)}$ (wherein n is 4 or 5), each of which can be used as a starting material for synthesizing the acyl group-containing hexaazaisowurtzitane derivative of the present invention, the arylmethyl group represented by B is an aryl group-substituted methyl group, and generally has 7 to 21 carbon atoms. A representative structure of the arylmethyl group B is represented by the following formula (XIII):

—$CH_2Ar$ (XIII)

wherein Ar represents an aromatic group having 6 to 20 carbon atoms.

The number of carbon atoms of the Ar in formula (XIII) above is generally in the range of from 6 to 20, preferably from 6 to 10, most preferably 6. Examples of Ar's include a phenyl group; alkylphenyl groups, such as a tolyl group (o-, m- and p-isomers), an ethylphenyl group (o-, m- and p-isomers), and a xylyl group; alkoxyphenyl groups, such as a methoxyphenyl group (o-, m- and p-isomers), an ethoxyphenyl group (o-, m- and p-isomers), and a butoxyphenyl group (o-, m- and p-isomers); and unsubstituted and substituted naphthyl groups. Of these, a phenyl group and alkoxy phenyl groups are preferred. In each of the $WB_6$ and $WA_nB_{(6-n)}$ (wherein n is 4 or 5), the arylmethyl groups may be the same or different.

The acyl group-containing hexaazaisowurtzitane derivative of the present invention represented by formula (I) $WA_tQ_{(6-t)}$ (wherein t is an integer of from 4 to 6) can be synthesized by various methods as described above.

The most characteristic feature of the methods for producing the acyl group-containing hexaazaisowurtzitane derivative of the present invention represented by formula (I) resides in that a reductive dearylmethylation reaction of a $WB_6$ is conducted in the presence of an acylating agent.

This reaction is represented by the following formula (11):

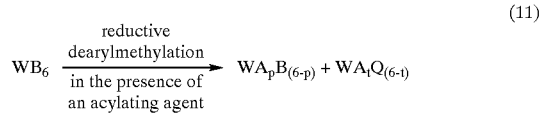

(11)

wherein p represents an integer of from 1 to 5, t represents an integer of from 4 to 6, B represents an arylmethyl group, A represents an acyl group having 1 to 10 carbon atoms, each Q independently represents a hydrogen atom or an alkyl group having 1 to 10 carbon atoms, and W represents a hexavalent hexaazaisowurtzitane residue.

The molar ratio of the $WA_pB_{(6-p)}$ to the $WA_tQ_{(6-t)}$ in the reaction mixture obtained by the reaction of formula (11) above is generally in the range of from 0.001 to 1,000, preferably from 0.01 to 100.

With respect to the solvent, reduction catalyst, acylating agent, reaction conditions and the like to be employed in the reaction of formula (11), those which are mentioned in connection with the reaction of formula (8) above can be employed.

In conducting the production of the acyl group-containing hexaazaisowurtzitane derivative of the present invention represented by formula (I-a) by subjecting $WB_6$ to reductive dearylmethylation in the presence of an acylating agent, it is important that a) formation of an N—H group by the reductive elimination of the arylmethyl group B, and b) formation of an N-acyl group by the acylation of the N—H group, are successively effected.

The above-mentioned formula (11) indicates that not only is $WA_pB_{(6-p)}$ (wherein p represents an integer of from 1 to 5) produced from $WB_6$, but also $WA_nH_{(6-n)}$ is produced by a further reaction of the $WA_pB_{(6-p)}$.

In the reaction of formula (11), the reductive dearylmethylation reaction is terminated when a reaction mixture [comprising $WA_pB_{(6-p)}$ and $WA_tQ_{(6-t)}$] having a desired composition has been obtained. Specifically, the advance of the dearylmethylation reaction is monitored by gas chromatography or liquid chromatography, and the reaction is terminated when a reaction mixture having a desired composition has been obtained.

Hereinbelow, an explanation is first given with respect to a presumed route of the reaction of formula (11), and then an explanation is given with respect to the utility and use of the reaction of formula (11).

The presumed route of the reaction of formula (11) is described in detail in the chart of the following formula (12). Since an N-alkyl group may be formed by the reduction (as a side reaction) of an N-acyl group, which reduction may occur depending on the reaction conditions, a by-produced, N-alkyl group-containing hexaazaisowurtzitane derivative is also described in the chart of formula (12). In the chart of formula (12), A represents an acyl group having 1 to 10 carbon atoms, B represents an arylmethyl group, R represents an alkyl group having 1 to 10 carbon atoms, H represents a hydrogen atom, and W represents a hexavalent hexaazaisowurtzitane residue.

Chart [formula (12)]

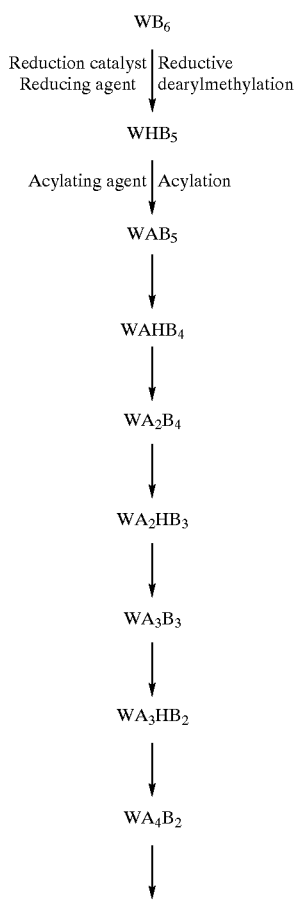
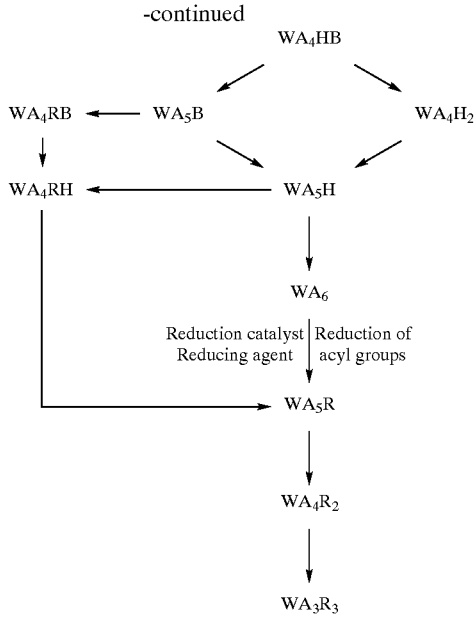

When the reaction of formula (11) is conducted in a batchwise manner, the proportions of reaction products obtained vary depending on the reaction time. When the reaction of formula (11) is conducted in a continuous manner, the proportions of reaction products obtained vary depending on the contact time. Further, the proportions of reaction products obtained may also vary depending on the types of the catalyst and solvent employed, the reaction temperature and the like. Therefore, in the reaction of formula (11), the proportions of reaction products can be varied in a desired ratio by appropriately selecting the reaction conditions.

The utility of the reaction of formula (11) is described below in detail.

When it is attempted to obtain the acyl group-containing hexaazaisowurtzitane derivative of the present invention from $WB_6$ by first subjecting $WB_6$ to reductive dearylmethylation in the absence of an acylating agent to obtain $WH_nB_{(6-n)}$ (wherein n represents an integer of from 1 to 6) and subsequently acylating the obtained $WH_nB_{(6-n)}$, the desired product cannot be obtained in high yield due to a decomposition of the W skeleton. The reason for this is presumed to reside in that secondary amino group-containing hexaazaisowurtzitane derivatives (such as $WHB_5$, $WH_2B_4$ and $WH_3B_3$) formed by the reductive dearylmethylation of $WB_6$ in the absence of an acylating agent are structurally unstable. By contrast, by the method of the present invention using the reaction of formula (11) in which the reductive dearylmethylation of $WB_6$ is conducted in the presence of an acylating agent, an acyl group-containing hexaazaisowurtzitane derivative can be synthesized without occurrence of the decomposition of the W skeleton. The reason for this is believed to reside in that, in the reaction of formula (11), unstable, secondary amino group-containing hexaazaisowurtzitane derivatives (such as $WHB_5$ and $WH_2B_4$) (which are produced in the early stage of the reaction) are immediately acylated and thus stabilized in the reaction system, so that the decomposition of the W skeleton can be suppressed, thereby allowing the dearylmethylation and acylation to further proceed.

As described above, the acyl group-containing hexaazaisowurtzitane derivative of the present invention represented by formula (I-a) can be synthesized in a single step by subjecting $WB_6$ to reductive dearylmethylation in the presence of an acylating agent. However, when it is attempted to complete the reaction in a single step, a wide variety of reaction products are formed at once and side reactions markedly occur. The present inventors have made studies to develop a method which can solve these problems and can produce $WA_tH_{(6-t)}$ (wherein t represents an integer of from 4 to 6) advantageously on a commercial scale and with high selectivity and in high yield. As a result, it has been found that, by conducting the above-mentioned reactions of formulae (8), (6) and (1) in this order, very good results can be obtained.

The following is a more detailed explanation of each of the reactions of formulae (8), (6) and (1).

I. The Reaction of Formula (8):

For producing $WA_nB_{(6-n)}$ in high yield in the above-mentioned reaction of formula (8), there can be employed various methods. Examples of such methods include:

1) a method in which the types and amounts of the reaction reagents are selected so that the reductive dearylmethylation reaction can terminate before completion;
2) a method in which the advance of the reductive dearylmethylation reaction is monitored by gas chromatography or liquid chromatography, and the reaction is terminated at an appropriate point in time; and
3) a method in which a solvent which is a good solvent for $WB_6$ but a poor solvent for $WA_nB_{(6-n)}$ (e.g., an aromatic compound, such as ethylbenzene or toluene) is used so as to cause $WA_nB_{(6-n)}$ produced by the reductive dearylmethylation of $WB_6$ to be precipitated from the reaction mixture.

Of methods 1), 2) and 3) above, method 3) is commercially most advantageous from the viewpoint of ease in operation.

In the reaction of formula (8), for suppressing side reactions to improve the selectivity for $WA_nB_{(6-n)}$, it is advantageous to use as an acylating agent a carboxylic ester of N-hydroxysuccinimide, such as N-acetoxysuccinimide, or a mixture of a carboxylic ester of N-hydroxysuccinimide and a carboxylic anhydride, such as acetic anhydride. When such an acylating agent is used, not only the selectivity for $WA_nB_{(6-n)}$ but also the yield of $WA_nB_{(6-n)}$ can be improved. The reason why the selectivity for $WA_nB_{(6-n)}$ is improved when a carboxylic ester of N-hydroxysuccinimide is used as an acylating agent has not yet been elucidated. However, it is believed that such a difference in the selectivity for $WA_nB_{(6-n)}$ between a carboxylic ester of N-hydroxysuccinimide and other acylating agents, such as a carboxylic anhydride, is ascribed to the difference in not only reactivity but also substrate specificity due to the steric restrictions (including specific three-dimensional structure and bulkiness) of the acylating agent.

The above fact that, when a carboxylic ester of N-hydroxysuccinimide is used as an acylating agent, the selectivity for $WA_nB_{(6-n)}$ can be remarkably improved has for the first time been found by the present inventors. This finding is very important for synthesizing $WA_nB_{(6-n)}$ with commercial advantages.

II. The Reaction of Formula (6):

When the reductive dearylmethylation of $WA_nB_{(6-n)}$ produced in the reaction of formula (8) is conducted in the presence of an acylating agent to synthesize $WA_6$, side reactions, such as formation of N-alkyl due to the reduction of N-acyl, are likely to occur, so that it becomes difficult to synthesize $WA_6$ with high selectivity.

By contrast, when the reductive dearylmethylation of $WA_nB_{(6-n)}$ is conducted in the absence of an acylating agent as shown by the reaction of formula (6), side reactions, such as formation of N-alkyl group, are suppressed, so that the reductive dearylmethylation reaction proceeds with high selectivity. This phenomenon has been found by the present inventors. From a reaction mixture obtained by the reductive dearylmethylation reaction of formula (6), high purity $WA_nH_{(6-n)}$ can be obtained in high yield by a simple isolation operation. Therefore, this reaction of formula (6) is very useful for synthesizing $WA_nH_{(6-n)}$.

As mentioned above, when the reductive dearylmethylation reaction of $WB_6$ is conducted in the absence of an acylating agent, the produced $WH_nB_{(6-n)}$ (wherein n represents an integer of from 1 to 6) is unstable in the reaction system, so that it is difficult to obtain $WH_nB_{(6-n)}$ in high yield. By contrast, as mentioned above, $WA_nH_{(6-n)}$ (wherein n represents an integer of from 4 to 5) is stable in the reaction system, so that $WA_nH_{(6-n)}$ can be synthesized in high yield.

The reason why $WH_nB_{(6-n)}$ (wherein n represents an integer of from 1 to 6) and $WA_nH_{(6-n)}$ (wherein n represents an integer of from 4 to 5) have different properties from each other, has not yet been elucidated. However, it is believed that a difference in properties between arylmethyl group B and acyl group A produces the difference in stability between the respective hexaazaisowurtzitane skeletons of $WH_nB_{(6-n)}$ and $WA_nH_{(6-n)}$.

The above-mentioned difference in properties between $WH_nB_{(6-n)}$ (wherein n represents an integer of from 1 to 6) and $WA_nH_{(6-n)}$ (wherein n represents an integer of from 4 to 5) has for the first time been found by the present inventors. Further, the hexaazaisowurtzitane compound represented by the formula $WA_nH_{(6-n)}$ (wherein n represents an integer of from 4 to 5) is not disclosed in any literature, and has for the first time been synthesized by the method of the present invention.

III. The Reaction of Formula (1):

As mentioned above under "prior art" herein, $WA_nH_{(6-n)}$ (wherein n represents an integer of from 4 to 5) as such can be advantageously used as various functional materials, such as a precursor of a polynitrohexaazaisowurtzitane derivative and a material for a highly polar polymer. If desired, $WA_nH_{(6-n)}$ (wherein n represents an integer of from 4 to 5) can be easily converted to $WA_6$ by effecting the reaction of formula (1).

$WA_6$ is not disclosed in any literature, and has for the first time been synthesized by the present inventors. $WA_6$ can also be advantageously used as various functional materials, as in the case of $WA_nH_{(6-n)}$ (wherein n represents an integer of from 4 to 5).

The acyl group-containing hexaazaisowurtzitane derivative of the present invention represented by the formula (I-a) $WA_tH_{(6-t)}$ (wherein t represents an integer of from 4 to 6) can be used as a starting material in the nitration reaction to thereby obtain a polynitrohexaazaisowurtzitane derivative.

The following explanation provides an example of methods for subjecting $WA_tH_{(6-t)}$ (n represents an integer of from 4 to 6) of the present invention to a nitration reaction for converting an N—H group and N—A group thereof to N—NO$_2$ groups.

An N—H group of the WA$_n$H$_{(6-n)}$ (wherein n represents an integer of from 4 to 5) of the present invention can be converted to an N—NO$_2$ group by various nitration methods. For example, WA$_n$H$_{(6-n)}$ (wherein n represents an integer of from 4 to 5) can be easily converted to WA$_n$(NO$_2$)$_{(6-n)}$ (wherein n represents an integer of from 4 to 5) in a single step. However, from the viewpoint of improving the yield of the desired WA$_n$(NO$_2$)$_{(6-n)}$, it is preferred to conduct the conversion of an N—H group to an N—NO$_2$ group by a method comprising two steps as shown in the reaction formula (13) below.

Illustratively, as shown in reaction formula (13) below, an N—H group of WA$_n$H$_{(6-n)}$ is nitrosated to an N—NO group, and the N—NO group is nitrated to an N—NO$_2$ group to thereby obtain WA$_n$(NO$_2$)$_{(6-n)}$.

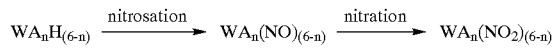

(13)

wherein n represents an integer of from 4 to 5, A represents an acyl group having 1 to 10 carbon atoms, H represents a hydrogen atom, (NO) represents a nitroso group, (NO$_2$) represents a nitro group, and W represents a hexavalent hexaazaisowurtzitane residue.

As a nitrosating agent used in the process of formula (13), any nitrosating agent can be employed as long as it is capable of nitrosating WA$_n$H$_{(6-n)}$ to produce WA$_n$(NO)$_{(6-n)}$. Generally, a mixture of sodium nitrite and an acid; dinitrogen tetraoxide; nitrosyl chloride and the like are used as nitrosating agents.

The nitrosation reaction temperature is generally in the range of from −50° C. to 200° C., preferably from −30° C. to 100° C., more preferably from −20° C. to 50° C.

As an oxidizing agent used in the nitration reaction in the process of formula (13), any oxidizing agent can be employed as long as it is capable of oxidizing a nitroso group to produce a nitro group. Generally, examples of oxidizing agents include nitric acid and hydrogen peroxide. Of these, nitric acid is preferred. These oxidizing agents can be used individually or in combination.

The oxidation reaction temperature is generally in the range of from −50° C. to 200° C., preferably from −30° C. to 150° C., more preferably from −20° C. to 60° C.

Also, an N—A group of the WA$_t$H$_{(6-t)}$ (wherein t represents an integer of from 4 to 6) of the present invention can be easily converted to an N—NO$_2$ group by nitration with nitric acid or a mixture of nitric acid and dinitrogen pentoxide as apparent from, for example, Example 21 (infra). For example, WA$_6$ can be converted to a polynitrohexaazaisowurtzitane derivative, such as WA$_4$(NO$_2$)$_2$, by various nitration methods, for example, using a mixture of nitric acid and dinitrogen pentoxide as a nitrating agent.

Further, as shown in the reaction formula (14) below, various hexaazaisowurtzitane derivatives represented by the formula WA$_n$E$_{(6-n)}$ can be nitrated to thereby obtain hexanitrohexaazaisowurtzitane [W(NO$_2$)$_6$].

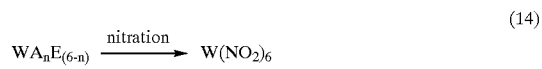

(14)

wherein n represents an integer of from 4 to 6, A represents an acyl group having 1 to 10 carbon atoms, E represents a nitroso group or a nitro group, and W represents a hexavalent hexaazaisowurtzitane residue.

As a nitrating agent to be used in converting an N—A group of WA$_n$E$_{(6-n)}$ to an N—NO$_2$ group, any nitrating agent can be employed as long as it is capable of converting an N—A group to an N—NO$_2$ group. For example, various nitrating agents containing nitric acid can be used. Illustrative examples of nitrating agents include nitrating agents containing a strong protonic acid, such as nitric acid/sulfuric acid nitrating agents or nitric acid/trifluoroacetic acid nitrating agents.

The reaction temperature for the reaction of formula (14) is generally in the range of from −50° C. to 120° C., preferably from −20° C. to 60° C.

The reaction time for the reaction of formula (14) is generally in the range of from 0.1 to 500 hours, preferably from 1 to 200 hours.

As described hereinabove, the N—H group and N—A group of the W skeleton are functional groups which can be easily converted to nitro groups. Therefore, by using WA$_t$H$_{(6-t)}$ (wherein t represents an integer of from 4 to 6) as an intermediate product, various polynitrohexaazaisowurtzitane derivatives can be produced in high yield.

As apparent from the above, according to the present invention, there is provided a method for producing a hexanitrohexaazaisowurtzitane represented by the following formula (IX):

(IX)

wherein NO$_2$ represents a nitro group and W represents a hexavalent hexaazaisowurtzitane residue represented by the following formula (II):

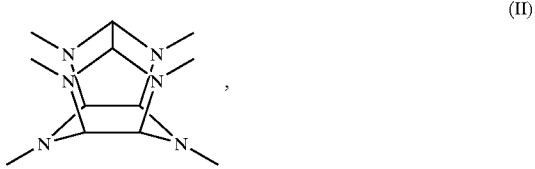

(II)

which comprises nitrating, with a nitrating agent, at least one compound selected from the group consisting of compounds which are, respectively, represented by the following formulae:

formula (III):

(III)

wherein each A independently represents an acyl group having 1 to 10 carbon atoms, and W is as defined above, formula (IV):

(IV)

wherein n represents an integer of from 4 to 5, H represents a hydrogen atom, and each of A and W is as defined above, formula (VII):

$$WA_n(NO)_{(6-n)} \quad (VII)$$

wherein NO represents a nitroso group, and each of n, A and W is as defined above, and formula (VIII):

$$WA_n(NO_2)_{(6-n)} \quad (VIII)$$

wherein each of n, A, $NO_2$ and W is as defined above.

The polynitrohexaazaisowurtzitane derivative prepared from the acyl group-containing hexaazaisowurtzitane derivative of the present invention can be advantageously used as an additive for modifying the properties of propellants and explosives, such as mechanical properties, detonation velocity, detonation pressure, burning rate, pressure exponent, sensitivity, heat resistance and the like, and also as a high performance material for explosives.

Described below are the advantages of the polynitrohexaazaisowurtzitane derivative prepared from the acyl group-containing hexaazaisowurtzitane derivative of the present invention.

For example, $WA_4(NO_2)_2$ has the following advantageous properties:

1) $WA_4(NO_2)_2$ has a similar molecular structure to that of a high performance explosive having a polynitramine group-containing cyclic structure, such as HNW, cyclotetramethylenetetranitramine (hereinafter referred to simply as "HMX") and cyclotrimethylenetrinitramine (hereinafter referred to simply as "RDX"), and exhibits excellent heat resistance as compared to HNW, HMX and RDX. [Even when $WA_4(NO_2)_2$ is used as an additive for propellants and explosives, there is no danger that it markedly lowers the heat resistance of the propellants and explosives.]

2) Differing from the above-mentioned nitramine compounds (i.e., HNW, HMX and RDX), $WA_4(NO_2)_2$ has not only an N-nitro group but also an N—A group in the skeleton thereof, so that it exhibits good affinity for a binder, such as polyurethane.

By adding the $WA_4(NO_2)_2$ having the above-mentioned advantageous properties to propellants and explosives comprising a nitramine compound (such as HNW, HMX, RDX or the like) and a binder, such as polyurethane, the adhesion between the solid component (i.e. nitramine compound) and the binder can be improved.

The $WA_4(NO_2)_2$ can be easily converted to HNW by nitration, so that it is useful as a raw material for producing HNW. HNW has a high density and high energy, so that it is very useful as an oxidizing agent for high performance explosives and smokeless propellants.

By reacting the tetraacylhexaazaisowurtzitane $WA_4H_2$ of the present invention with a dicarboxylic acid derivative, such as a dicarboxylic halide or dicarboxylic diester, a highly polar polymer having a hexaazaisowurtzitane skeleton in the main chain thereof can be obtained.

In synthesizing the acyl group-containing hexaazaisowurtzitane derivative $WA_nH_{(6-n)}$ (wherein n represents an integer of from 4 to 6) of the present invention, by using an acylating agent having a specific functional group, a crosslinkable polyacylhexaazaisowurtzitane can be obtained.

The $WA_nH_{(6-n)}$ (wherein n represents an integer of from 4 to 6) of the present invention as such can also be used as additives, such as a polymer modifier.

Hereinbelow is given a flow chart showing preferred modes of the production methods involved in the present invention.

Flow Chart
Preferred Modes of Production
Methods involved in The Present Invention

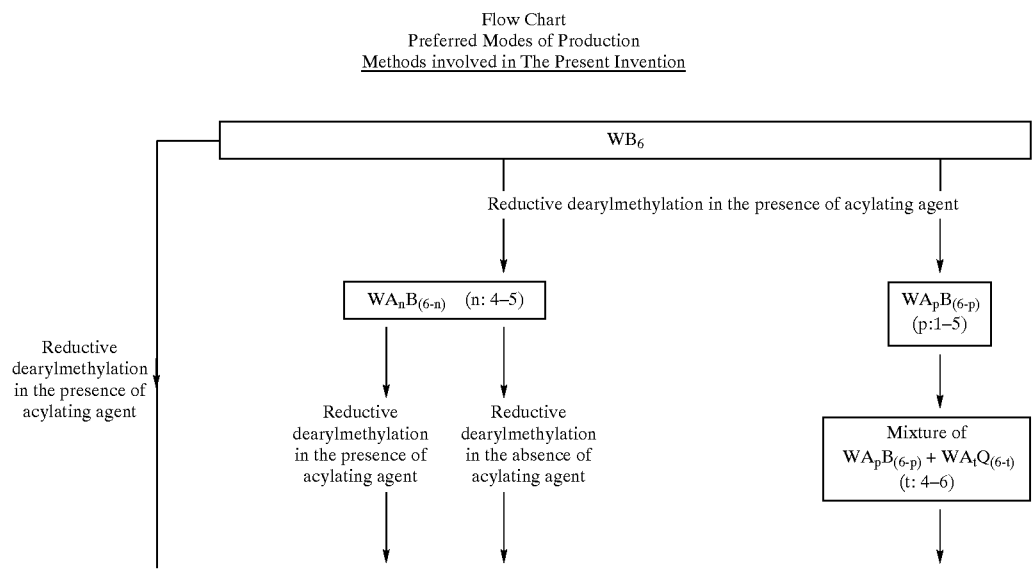

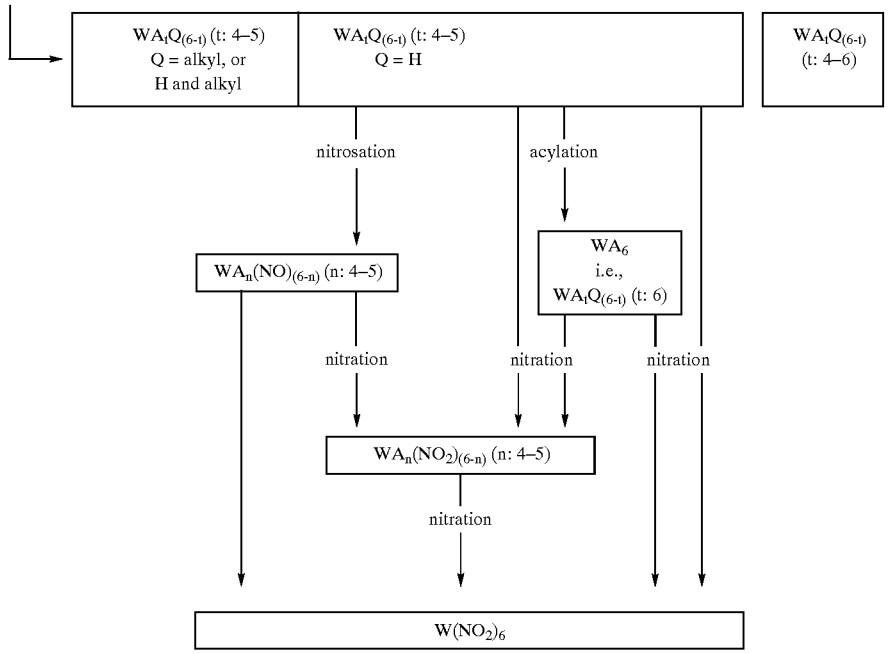

Meanings of symbols in the chart
W: hexavalent hexaazaisowurtzitane residue
B: arylmethyl group
A: $C_1$–$C_{10}$ acyl group
Q: hydrogen atom and/or $C_1$–$C_{10}$ alkyl group
NO: nitroso group
$NO_2$: nitro group As can be seen from the above flow chart, the acyl group-containing hexaazaisowurtzitane derivative $WA_tQ_{(6-t)}$ (wherein W is a hexavalent hexaazaisowurtzitane residue, each Q is independently a hydrogen atom or a $C_1$–$C_{10}$ alkyl group and t is from 4 to 6) of the present invention can be produced from a hexakis(arylmethyl) hexaazaisowurtzitane $WB_6$ (wherein W is as defined above and B is a $C_7$–$C_{21}$ arylmethyl group), directly or through an acyl group- and arylmethyl group-containing hexaazaisowurtzitane derivative $WA_nB_{(6-n)}$ (wherein W and B are as defined above and n is 4 or 5) or $WA_pB_{(6-p)}$ (wherein W and B are as defined above and p is from 1 to 5). The acyl group-containing hexaazaisowurtzitane derivative $WA_tQ_{(6-t)}$ (wherein W, A, Q and t are as defined above) can be easily converted to hexanitrohexaazaisowurtzitane $W(NO_2)_6$ (wherein W is as defined above) in high yield, directly or through a nitroso group-containing hexaazaisowurtzitane derivative $WA_n(NO)_{(6-n)}$ (wherein W and A are as defined above and n is 4 or 5) and/or a nitro group-containing hexaazaisowurtzitane derivative $WA_n(NO_2)_{(6-n)}$ (wherein W and A are as defined above and n is 4 or 5).

EXAMPLES

Hereinbelow, the present invention is described in more detail with reference to Examples and Comparative Examples, which should not be construed as limiting the scope of the present invention.

Various measurements were conducted in accordance with the following methods.

(1) $^1$H-NMR:
JNM-FX-200 (manufactured and sold by JEOL LTD., Japan) was used.

(2) $^{13}$C-NMR:
JNM-GX-400 (manufactured and sold by JEOL LTD., Japan) was used.

(3) $^{13}$C-$^1$H COSY ($^{13}$C-$^1$H shift correlation NMR):
JNM-GX-400 was used. In this method, an interaction between $^{13}$C and $^1$H is measured. By this method, when a peak ascribed to either $^{13}$C or $^1$H is identified, the chemical shift of either $^1$H having $^{13}$C bonded thereto or the $^{13}$C having the $^1$H bonded thereto can be determined.

(4) EI (Electron Impact)—mass spectrometry:
HP 5790B (manufactured and sold by Hewlett Packard Company, U.S.A.) was used.

(5) GC (Gas Chromatography)—mass spectrometry:
1) HP5890A (manufactured and sold by Hewlett Packard Company, U.S.A.) was used.
2) Column: Metallic capillary column, 0.25 mm (inner diameter)×15 m, Ultra ALLOY (HT) (column for use under high temperature conditions), thickness of a film coated on the inner wall of the capillary: 0.15 µm
3) Temperature: Column; the temperature was elevated from 100° C. to 340° C. at a temperature elevation rate of 20° C./min. and the temperature was maintained at 340° C. for 20 min.
Inlet hole; 340° C.
GC/MS joint; 340° C.
4) Carrier gas: Helium (flow rate of helium gas introduced to the apparatus; 100 ml/min, Column pressure; 100 kPa)

(6) FD (Field Desorption)—mass spectrometry
JEOL HX-110 (manufactured and sold by JEOL LTD., Japan) was used. Several pg of a sample was dissolved in about 10 μl of methanol to thereby obtain a solution. Several μl of the obtained solution was coated on an emitter, and a measurement was conducted.

(7) Infrared absorption spectrometry

A measurement was conducted by the KBr tablet method, using FT/IR-5M (manufactured and sold by Japan Spectroscopic Co., Ltd., Japan)

(8) Differential Scanning Calorimeter (DSC)

DSC-220 (manufactured and sold by Seiko Instruments Inc., Japan) was used.

(9) High performance liquid chromatography

A measurement was conducted under the following conditions by using the below-described apparatus.

1) Apparatus: 610 ISOCRATIC SYSTEM (manufactured and sold by Waters Assoc. Co., U.S.A.)
① 600 controller
② 600E pump
③ 486 Tunable Absorbance Detector 2) Column: μ-Bondasphere (manufactured and sold by Waters Assoc. Co., U.S.A.)

| | | |
|---|---|---|
| ① | particle diameter | 5 μm |
| ② | packing material | C18 |
| ③ | pore size | 100 Å |
| ④ | column size | 3.9 mm × 15 cm |

3) Mobile phase liquid:
acetonitrile/water: 60/40

4) Flow rate: 0.5 ml/min

5) Column temperature: 40° C.

Example 1

Synthesis of $WA_6$ by Acetylation of $WA_4H_2$ 1.0 g (2.98 mmol) of tetraacetylhexaazaisowurtzitane was dissolved in 100 ml of acetic anhydride. To the resultant solution was added 5 g (63.7 mmol) of acetyl chloride, and the resultant mixture was stirred for 1 hour to perform a reaction thereof. Subsequently, the solvent was distilled off under reduced pressure from the resultant reaction mixture to obtain a residue. The obtained residue was dissolved in ethyl acetate. To the resultant solution was added hexane to obtain a precipitate, which was 1.16 g of a white mass of hexaacetylhexaazaisowurtzitane (yield: 93%).

The obtained hexaacetylhexaazaisowurtzitane was placed in a sublimation apparatus, and then the apparatus was immersed in a 270° C. oil bath. It was confirmed that the hexaacetylhexaazaisowurtzitane can be sublimated under a reduced pressure of 10 mmHg.

Results of the analysis of hexaacetylhexaazaisowurtzitane are as follows.

Results of $^1$H-NMR [solvent: $CDCl_3$; standard: tetramethylsilane (hereinbelow frequently referred to as "TMS"); measurement temperature: 60° C.; unit: δ (ppm)]: 2.05 (s, 6H, $COCH_3$), 2.14 (s, 6H, $COCH_3$), 2.41 (s, 6H, $COCH_3$), 6.42 (s, 2H, CH), 6.48 (d, 2H, CH), and 6.94 (d, 2H, CH).

By $^1$H-NMR, 6 hydrogen atoms of the W skeleton and 6 acetyl groups could be identified.

Results of $^{13}$C-NMR [solvent: $CDCl_3$; standard: TMS; unit: δ (ppm)]: 20.74 ($CH_3$), 21.55 ($CH_3$), 61.09 (CH), 66.55 (CH), 72.17 (CH), 167.60 (C=O), 168.31 (C=O) and 169.79 (C=O).

By $^{13}$C-NMR, the carbon atom of a methyl group and the carbon atom of a carbonyl group, each of the groups belonging to the acetyl group, and carbon atoms on the W skeleton could be identified.

By $^{13}$C-$^1$H COSY, $^{13}$C's bonded to respective $^1$H's identified by the above $^1$H-NMR could be identified.

Results of EI-mass spectrometry (m represents the molecular weight of a parent molecule): 420 (5%, m/z), 377 [5%, (m minus molecular weight of $COCH_3$)/z], 335 (10%), 295 (15%), 208 (12%), 165 (10%), 123 (12%) and 43 (100%, $COCH_3$).

By EI-mass spectrometry, a parent ion peak (420) of hexaacetylhexaazaisowurtzitane, an ion peak (377) ascribed to a residual molecule which has a structure assumed by removal of one acetyl group from the parent molecule, and an ion peak (43) ascribed to the acetyl group could be identified.

The results of infrared absorption spectrometry by KBr method showed an absorption around 1660 $cm^{-1}$, wherein the absorption is ascribed to the stretching vibration of a carbonyl group (C=O) of the acetyl group.

Example 2

Synthesis of $WA_6$ from $WA_4B_2$ 3.67 g (7.11 mmol) of tetraacetyldibenzylhexaazaisowurtzitane, 1.6 g (7.11 mmol) of $Pd(OAc)_2$ as a reduction catalyst and 150 ml of acetic acid were charged, together with a stirring element, into a 300 ml microbomb. The bomb was purged with nitrogen gas. Then, hydrogen gas was introduced into the bomb so that the internal pressure of the bomb became 5 $kgf/cm^2$-G, and then the contents of the bomb were stirred for 15 hours to perform a reaction thereof. The resultant reaction mixture was taken out from the bomb and subjected to filtration to remove the catalyst. Then, the resultant filtrate was subjected to distillation under reduced pressure to distill off the solvent, thereby obtaining a solid residue. The obtained solid residue was washed with 100 ml of ethyl acetate. The resultant white solid residue was dissolved in 200 ml of acetic anhydride. To the resultant solution was added 5 g (63.7 mmol) of acetyl chloride, and the resultant mixture was stirred for 1 hour. Subsequently, the solvent was distilled off under reduced pressure from the mixture. The resultant residue was recrystallized from toluene, to thereby obtain 2.09 g of a white mass of hexaacetylhexaazaisowurtzitane (yield: 70%).

Example 3

Synthesis of $WA_6$ from $WA_4B_2$, in which the Reaction Mixture Obtained by the Reductive Dearylmethylation is in situ Subjected to Acetylation Without the Removal of the Catalyst and the Solvent The reductive dephenylmethylation of tetraacetyldibenzylhexaazaisowurtzitane was conducted in substantially the same manner as in Example 2, to thereby obtain a reaction mixture containing the reduction catalyst and the solvent. To the reaction mixture was added 5 g (63.7 mmol) of acetyl chloride (acetylating agent) and the resultant mixture was stirred for 3 hours to perform a reaction thereof. The resultant reaction mixture was subjected to filtration, to thereby remove the catalyst. The resultant filtrate was subjected to distillation under reduced pressure to distill off the solvent. The resultant solid residue was recrystallized from toluene, to thereby obtain 1.92 g of a white mass of hexaacetylhexaazaisowurtzitane (yield: 64%).

Example 4

Synthesis of $WA_6$ from $WB_6$ 1.89 g (2.66 mmol) of hexabenzylhexaazaisowurtzitane, 1.70 g (1.60 mg-atom) of Pd-C (Pd content: 10%) as a reduction catalyst, 5.0 g (31.8 mmol) of N-acetoxysuccinimide (acetylating agent), 160 ml of ethylbenzene and 3.24 g (31.8 mmol) of acetic anhydride (acetylating agent) were charged, together with a stirring element into a 300 ml microbomb. The bomb was purged with hydrogen gas. Then, hydrogen gas was introduced into the bomb so that the internal pressure of the bomb became 10 kg/cm$^2$-G, and then the bomb was immersed in a 60° C. oil bath. Then, the contents of the bomb were stirred for 40 hours to perform a reaction thereof. The resultant reaction mixture was allowed to cool to room temperature. Subsequently, the reaction mixture containing $WA_nB_{(6-n)}$ (wherein n is 4 or 5) as a precipitate was taken out from the bomb and subjected to filtration to filter off the precipitate and the reduction-catalyst. The obtained precipitate, the recovered reduction catalyst and 50 ml of acetic acid as a solvent were charged into a 300 ml microbomb. Hydrogen gas was introduced into the bomb so that the internal pressure of the bomb became 5 kg/cm$^2$-G, and the contents of the bomb were stirred for 20 hours to perform a reaction thereof. After completion of the reaction, 5 g (63.7 mmol) of acetyl chloride was added to the resultant reaction mixture, and the mixture was stirred for 1 hour. The resultant mixture was subjected to distillation under reduced pressure to distill off the solvent, thereby obtaining a solid residue. 200 ml of chloroform was added to the obtained solid residue, so that the solid residue comprised mainly of $WA_6$ was dissolved in the chloroform. The resultant solution was subjected to filtration, to thereby remove the catalyst. The resultant filtrate was subjected to distillation under reduced pressure, to thereby distill off the solvent. The resultant residue was recrystallized from toluene to obtain 0.50 g of a white mass of hexaacetylhexaazaisowurtzitane (yield: 45%).

Example 5

Synthesis of $WA_nH_{(6-n)}$ and $WA_6$ from $WB_6$

The reductive debenzylation of hexabenzylhexaazaisowurtzitane in the presence of the acetylating agents was conducted in substantially the same manner as in Example 4, to thereby obtain a reaction mixture containing $WA_nB_{(6-n)}$ (wherein n is 4 or 5). After completion of the reaction, the reaction mixture containing a precipitate was taken out from the bomb and subjected to filtration by using a filter paper, to filter off the precipitate and the reduction catalyst. The precipitate on the filter paper was treated in situ with 200 ml of chloroform to dissolve the precipitate therein. The filtrate (which contained the chloroform used for the treatment) was subjected to distillation to distill off the solvent (ethylbenzene and chloroform). The resultant solid residue was dissolved in 200 ml of chloroform to obtain a solution. To the solution was added an aqueous 28% solution of ammonia, and the resultant mixture was vigorously stirred for 30 minutes, so that the reaction mixture was separated into an aqueous phase and a chloroform phase, wherein the N-acetoxysuccinimide was decomposed and moved into the aqueous phase. The chloroform phase was isolated and subjected to distillation to distill off the solvent (chloroform). The resultant white solid residue was dissolved in 50 ml of acetic acid. To the resultant solution was added 0.6 g (2.66 mmol) of Pd(OAc)$_2$ as a reduction catalyst. The solution containing the reduction catalyst was charged into a 100 ml microbomb. Hydrogen gas was introduced into the bomb so that the internal pressure of the bomb became 5 kgf/cm$^2$-G, and the contents of the bomb were stirred for 20 hours to perform a reaction thereof. (The yield of hexaacetylhexaazaisowurtzitane at this point in timer was 0.3%, as measured by gas chromatography.) 5 g (63.7 mmol) of acetyl chloride was added to the reaction mixture, and the resultant mixture was stirred for 1 hour. Subsequently, the solvent (acetic acid) was distilled off from the mixture to obtain a solid residue. 200 ml of chloroform was added to the obtained solid residue. The resultant solution was subjected to filtration, to thereby remove the catalyst. The resultant filtrate was subjected to distillation to distill off the solvent, thereby obtaining a solid residue. The obtained solid residue was recrystallized from toluene, to thereby obtain 0.39 g of hexaacetylhexaazaisowurtzitane (yield: 35%). This indicates that hexaazaisowurtzitane compounds having a secondary amino group, such as tetraacetylhexaazaisowurtzitane and pentaacetylhexaazaisowurtzitane, had been formed prior to the addition of the acetyl chloride and that such compounds having a secondary amino group had been converted to hexaacetylhexaazaisowurtzitane by the addition-of acetyl chloride.

Example 6

Synthesis of $WA_4Et_2$ (Wherein Et Represents an Ethyl Group) from $WA_4B_2$ 0.50 g (0.97 mmol) of tetraacetyldibenzylhexaazaisowurtzitane, 0.21 g (0.19 mg-atom) of Pd-C (Pd content: 10%) as a reduction catalyst, 2.37 g (23.3 mmol) of acetic anhydride (acetylating agent) and 50 ml of acetic acid were charged, together with a stirring element into a 100 ml microbomb. The bomb was purged with hydrogen gas. Then, hydrogen gas was introduced into the bomb so that the internal pressure of the bomb became 50 kgf/cm$^2$-G. Then, the contents of the bomb were stirred for 15 hours to perform a reaction thereof. After completion of the reaction, the resultant reaction mixture was taken out from the bomb and subjected to filtration to filter off the reduction catalyst. The resultant filtrate was subjected to distillation, to thereby distill off the solvent (acetic acid). The resultant solid residue was reprecipitated from a mixture of chloroform and hexane to perform a purification, thereby obtaining a white mass of diethyltetraacetylhexaazaisowurtzitane. The reaction conditions and the yield are shown in Table 1.

Results of the analysis of the diethyltetraacetylhexaazaisowurtzitane are as follows.

Results of EI-mass spectrometry: 392 (1%, m/z), 278 (1%), 236 (10%) 193 (25%), 138 (30%), 109 (45%), 97 (20%), 81 (81%), 69 (60%), 56 (20%), 43 (100%, COCH$_3$), 29 (20%, CH$_2$CH$_3$), 28 (52%) and 15 (20%, CH$_3$).

By EI-mass spectrometry, a parent ion peak (392) of tetraacetyldiethylhexaazaisowurtzitane, an ion peak (43) of acetyl group and an ion peak (29) of ethyl group were identified.

Results of $^1$H-NMR spectrometry [solvent: CDCl$_3$; standard: TMS; unit: δ (ppm)] 1.25 (t, 6H, CH$_3$ of ethyl group), 2.14 (S, 12H COCH$_3$), 2.90 (m, 4H, CH$_2$ of ethyl group), 5.20 (d, 2H, CH), 5.74 (d, 2H, CH) and 6.40 (S, 2H, CH).

By $^1$H-NMR spectrum, a methine group of the W skelton an ethyl group and an acetyl group could be identified.

Examples 7 Through 12

Synthesis of $WA_6$ and $WA_4R_2$ from $WA_4B_2$ by the Reductive Dearylmethylation in the Presence of an Acylating Agent, and Observations on the Variation in the Amount Ratio of the Produced $WA_6$ to the Produced $WA_4R_2$ Depending on the Reaction Conditions In Examples 7 through 12, reactions were conducted in substantially the same manner as in Example 6, except that the type and amount of acylating agent, the type of solvent, the type and amount of catalyst, the hydrogen pressure and the reaction time were varied. The reaction conditions and the yields of the reaction products are shown in Table 1.

As shown in Table 1, various catalysts can be used for producing hexaacetylhexaazaisowurtzitane and diethyltetraacetylhexaazaisowurtzitane.

Results of EI-mass spectrometry of diethyltetraacetylhexaazaisowurtzitane: 392 (1%, m/z), 278 (1%), 236 (10%), 193 (25%), 138 (30%), 109 (45%), 97 (20%), 81 (81%), 69 (60%), 56 (20%), 43 (100%, $COCH_3$), 29 (20%, $CH_2CH_3$), 28 (52%) and 15 (20%, $CH_3$).

Results of EI-mass spectrometry of hexaacetylhexaazaisowurtzitane: 420 (5%, m/z), 377 (5%, [m minus molecular

TABLE 1

| Example | Acylating agent (amount)[1] | Catalyst (amount)[2] | Pressure of hydrogen ($kgf/cm^2$-G) | Reaction time (hour) | Yield[5] $WA_6$ (%) | $WA_4Et2$ (%) |
|---|---|---|---|---|---|---|
| 6 | $Ac_2O$ (12) | 10% Pd—C (10) | 50 | 15 | 0.2 | 92.0 |
| 7 | $Ac_2O$ (12) | 10% Pd—C (10) | 5 | 10 | 4.3 | 46.8 |
| 8 | $Ac_2O$ (12) | 10% Pd—C (1) | 5 | 531 | 15.1 | 5.1 |
| 9 | $Ac_2O$ (12) | PdO (112) | 50 | 40 | 2.7 | 15.1 |
| 10 | $Ac_2O$ (12) | 10% Pd—C[4] (10) | 50 | 17 | 1.8 | 55.0 |
| 11 | $Ac_2O$ (6) + NAS (6)[3] | 10% Pd—C (10) | 50 | 16 | 4.5 | 35.3 |
| 12 | $Ac_2O$ (12) | 5% Pd—$Al_2O_3$ (10) | 50 | 15 | 3.7 | 45.4 |

[1]The number shown in the parenthes is the equimolar amount of an acylating agent to benzyl groups of $WB_6$ used. For example, 12 equivalents means 23.3 mmol.
[2]The number shown in the parenthes is the mole % of a catalyst, based on the mole of benzyl groups of $WB_6$ used.
[3]NAS represents N-acetoxysuccinimide.
[4]10% Pd—C was treated with acetic anhydride prior to use.
[5]Yields were measured by gas chromatography.
[6]In Table 1, Ac represents an acetyl group and Et represents an ethyl group.

Example 13

Synthesis of Various Acetyl Group-containing Hexaazaisowurtzitane Derivatives, such as $WA_4B_2$ and $WA_5B$, by the Reductive Dearylmethylation of $WB_6$ in the Presence of an Acylating Agent The reductive debenzylation of hexabenzylhexaazaisowurtzitane in the presence of an acetylating agent was conducted in substantially the same manner as in Example 4, except that the reaction was conducted under conditions such that the pressure in the bomb was 50 $kgf/cm^2$-G, the reaction temperature was room temperature and the reaction time was 200 hours.

After completion of the reaction, the analysis of the reaction products in the reaction mixture was conducted by GC-mass spectrometry. As a result, it was found that the reaction mixture contained the following compounds: tetraacetyldibenzylhexaazaisowurtzitane, pentaacetylbenzylhexaazaisowurtzitane, hexaacetylhexaazaisowurtzitane, ethylpentaacetylhexaazaisowurtzitane and diethyltetraacetylhexaazaisowurtzitane. The yield of each of the above compounds was measured by gas chromatography. As a result, the yield of each of the compounds was as follows: tetraacetyldibenzylhexaazaisowurtzitane; 70%; pentaacetylbenzylhexaazaisowurtzitane 6.2%; hexaacetylhexaazaisowurtzitane: 0.9%; ethylpentaacetylhexaazaisowurtzitane: 1.3%; and diethyltetraacetylhexaazaisowurtzitane: 1.1% The results of EI-mass spectrometry of these compounds are as follows.

Results of EI-mass spectrometry of pentaacetylbenzylhexaazaisowurtzitane: 468 (2%, m/z), 425 (3%, [m minus molecular weight of $COCH_3$]/Z), 255 (12%), 91 (66%, $CH_2Ph$) and 43 (100%, $COCH_3$).

Results of EI-mass spectrometry of ethylpentaacetylhexaazaisowurtzitane: 406 (1%, m/z), 363 (1%, [m minus molecular weight of $COCH_3$]/Z), 278 (2%), 236 (5%), 193 (10%), 109 (12%), 43 (100%, $COCH_3$), 29 (15%, $CH_2CH_3$) and 15 (8%, $CH_3$).

weight of $COCH_3$]/Z), 335 (10%), 295 (15%), 208 (12%), 165 (10%), 123 (12%) and 43 (100%, $COCH_3$).

Example 14

Reductive Dearylmethylation of $WB_6$ in the Presence of an Acylating Agent Using Only a Carboxylic Anhydride as an Acylating Agent, Without Using a Carboxylic Ester of N-Hydroxysuccinimide as an Acylating Agent The reductive debenzylation was conducted in substantially the same manner as in Example 13, except that only 32.4 g of acetic anhydride was used as an acetylating agent without using N-acetoxysuccinimide. During the course of the reaction, a sample of the reaction mixture was taken. The composition of the sample was analyzed by FD-mass spectrometry. As a result, it was found that the sample contained, as intermediate compounds, diacetyltetrabenzylhexaazaisowurtzitane ($M^+612$) and triacetyltribenzylhexaazaisowurtzitane ($M^+564$). Also, it was found that the sample contained, as a compound having at least one acetyl group removed by reduction, ethyldiacetyltribenzylhexaazaisowurtzitane ($M^+550$), ethyltriacetyldibenzylhexaazaisowurtzitane ($M^+502$) and diethyldiacetyldibenzylhexaazaisowurtzitane ($M^+488$).

After completion of the reaction, the yield of each of the reaction products in the resultant reaction mixture was measured by gas chromatography. As a result, the yield of each of the reaction products was as follows: triacetyltribenzylhexaazaisowurtzitane: 13%; ethyldiacetyltribenzylhexaazaisowurtzitane: 3.1%; tetraacetyldibenzylhexaazaisowurtzitane: 7.5%; ethyltriacetyldibenzylhexaazaisowurtzitane: 32%; diethyldiacetyldibenzylhexaazaisowurtzitane: 30%; pentaacetylbenzylhexaazaisowurtzitane: 1.6%; ethyltetraacetylbenzylhexaazaisowurtzitane: 1.1%; diethyltriacetylbenzylhexaazaisowurtzitane: 6.2%; hexaacetylhexaazaisowurtzitane: 0.5%; ethylpentaacetylhexaazaisowurtzitane: 1.2%; and diethyltetraacetyl-hexaazaisowurtzitane: 1.1%.

The above results show that, when a carboxylic ester of N-hydroxysuccinimide is not used as an acylating agent, the conversion by reduction of an acyl group to an alkyl group markedly occurs.

Example 15

Reductive Dearylmethylation of $WB_6$ in the Presence of an Acylating Agent, Using Only N-Acetoxysuccinimide as an Acylating Agent The reductive debenzylation was conducted in substantially the same manner as in Example 13, except that 7.5 g of N-acetoxy succinimide was used as an acetylating agent without using acetic anhydride.

During the course of the reaction, a sample of the reaction mixture was taken. The composition of the sample was analyzed by FD-mass spectrometry. As a result, it was found that the sample contained, as intermediate compounds, pentabenzylhexaazaisowurtzitane ($[M+H]^+$ 619), acetyl-pentabenzylhexaazaisowurtzitane ($M^+$660), diacetyltetra-benzylhexaazaisowurtzitane ($M^+$612) and triacetylbenzyl-hexaazaisowurtzitane ($M^+$564). After the completion of the reaction, the yield of each of the reaction products was measured by gas chromatography. The yield of each of the reaction products was as follows: diacetyltetrabenzyl-hexaazaisowurtzitane: 74%; triacetyltribenzylhexaazai-sowurtzitane: 15%; and tetraacetylbenzylhexaazai-sowurtzitan: 3%.

The above results show that when only a carboxylic ester of N-hydroxysuccinimide is used as an acylating agent in the reductive dearylmetilation of $WB_6$, the conversion by reduction of an acyl group of $WA_nB_{6-n}$ (in which n is an integer of from 1 to 4) to an alkyl group during the course of the successive dearylmethylations of $WB_6$ to $WA_nB_{6-n}$ (in which n is integer of from 1 to 5) can be suppressed. However, the results also show that the reaction rate of the above reaction is lower than that of the reaction conducted using, as an acylating agent, a mixture of a carboxylic ester of N-hydroxysuccinimide and a carboxylic anhydride.

Example 16

Synthesis of $WA_4H_2$ from $WA_4B_2$ 3.67 g (7.11 mmol) of tetraacetyldibenzylhexaazaisowurtzitane, 1.60 g (7.11 mmol) of $Pd(OAc)_2$ as a reduction catalyst and 150 ml of acetic acid as a solvent were charged, together with a stirring element, into 300 ml microbomb, and the bomb was purged with nitrogen gas. Then, hydrogen gas was introduced into the bomb so that the internal pressure of the bomb became 5 kg/cm$^2$-G, and the contents of the bomb were then stirred for 15 hours to perform a reaction thereof. The reaction mixture was taken out from the microbomb and was subjected to filtration to filter off the catalyst. The resultant filtrate was subjected to distillation to distill off the solvent under reduced pressure. The resultant solid residue was washed with 100 ml of ethyl acetate and then 1.67 g of a white mass of tetraacetylhexaazaisowurtzitane was obtained (yield: 71%).

Results of the analysis of the obtained tetraacetyl-hexaazaisowurtzitane are as follows.

Results of $^1$H-NMR spectrometry [solvent: $D_2O$; standard: TMS; unit: δ (ppm)]: 1.98 (s, 6H, $COCH_3$), 2.00 (s, 6H, $COCH_3$) 5.29 (m, 2H, CH), 5.50 (m, 2H, CH) and 6.35 (m, 2H, CH).

By $^1$H-NMR, a methine group of the W skeleton and 4 acetyl groups could be identified.

The results of infrared absorption spectrometry showed two absorptions within the range of 3300–3400 cm$^{-1}$, each of which is ascribed to the stretching vibration of secondary amino group (N—H group), and also showed an absorption around 1660 cm$^{-1}$, which is ascribed to the stretching vibration of a carbonyl group (C=O) of the acetyl group. The above results show that the W skeleton has, as substituents, acetyl groups and N—H groups.

Example 17

Synthesis of $WA_4H_2$ from $WA_4B_2$, Conducted Using a Catalyst Which is Different from that Used in Example 16 at a Reaction Temperature Which is Different from that Employed in Example 16

1.20 g (2.33 mmol) of tetraacetyldibenzylhexaazaisowurtzitane, 0.496 g (0.466 mol) of Pd-C (Pd content 10%) as a reaction catalyst and 60 ml of acetic acid (solvent) were charged, together with a stirring element, into 300 ml microbomb, and the bomb was purged with nitrogen gas. Then, hydrogen gas was introduced into the microbomb so that the internal pressure of the bomb became 3 kgf/cm$^2$-G, and then the microbomb was immersed in a 40° C. oil bath. Then, the contents of the microbomb were stirred for 5 hours using a stirrer to perform a reaction thereof. The reaction mixture was taken out from the microbomb and subjected to filtration to filter off the catalyst. The resultant filtrate was subjected to distillation under reduced pressure to distill off the solvent. The resultant solid residue was washed with 100 ml of ethyl acetate, to thereby obtain 0.57 g of a white mass of tetraacetyl-hexaazaisowurtzitane.

The above results show that even when the reaction was conducted using a catalyst which is different from that used in Example 16 at a temperature which is different from that employed in Example 16, $WA_4H_2$ can be produced as in Example 16.

Example 18

Confirmation of the Formation of $WA_nH_{(6-n)}$ During the Course of Reductive Dearylmethylation of $WB_6$ in the Presence of an Acylating Agent The reductive debenzylation of hexabenzylhexaazai-sowurtzitane in the presence of the acetylating agents was conducted in substantially the same manner as in Example 4, except that the reaction time was 200 hours. After completion of the reaction, the reaction mixture was analyzed by gas chromatography. As a result, it was found that the yield of hexaacetylhexaazaisowurtzitane was only 0.8%. On the other hand, the presence of tetraacetylhexaazai-sowurtzitane ($WA_4H_2$) was identified by high performance liquid chromatography. To the above-mentioned reaction mixture was added acetyl chloride, and then the resultant mixture was stirred for 1 hour to perform a reaction thereof. The resultant reaction mixture was analyzed by gas chromatography. Results of the analysis show that the yield of hexaacetylhexaazaisowurtzitane was 5%. This also indicates that $WA_nH_{(6-n)}$, such as tetraacetylhexaazaisowurtzitane and pentaacetylhexaazaisowurtzitane, had been present in the reaction system prior to the addition of the acetylchloride.

Example 19

Synthesis of $WA_4B_2$ by Reductive Dearylmethylation of $WB_6$ in the Presence of an Acylating Agent 1.89 g (2.66 mmol) of hexabenzylhexaazaisowurtzitane, 1.70 g (1.6 mg-atom) of Pd-C (Pd content: 10%) as a reduction catalyst, 5.0 g (31.8 mmol) of N-acetoxysuccinimide (acetylating agent), 160 ml of ethylbenzene (solvent) and 3.24 g (31.8 mmol) of acetic anhydride (acetylating agent) were charged, together with a stirring element, into a 300 ml microbomb. The bomb was purged with hydrogen gas. Then, hydrogen gas was introduced into the bomb so that the internal pressure of the bomb became 50 kg/cm$^2$-G, and then the contents in the bomb were stirred for 20 hours using a stirrer to perform a reaction thereof. The resultant reaction mixture was taken out from the bomb and subjected to filtration by using a filter paper to filter off a precipitate and the reduction catalyst. The precipitate on the filter paper was treated in situ with 200 ml of chloroform to dissolve the precipitate therein. The filtrate (which contained chloroform used for the treatment) was subjected to distillation to distill off the solvent. The resultant solid residue was dissolved in 200 ml of chloroform to obtain a solution. To the solution was added 200 ml of an aqueous 28% solution of ammonia, and the resultant mixture was vigorously stirred for 30 minutes, so that the reaction mixture was separated into an aqueous phase and a chloroform phase, wherein the N-acetoxy succinimide was decomposed and moved into the aqueous phase. The chloroform phase was isolated and subjected to distillation to distill off the solvent, thereby obtaining 1.29 g of a white solid residue. The white solid residue obtained was recrystallized from ethylbenzene, to thereby obtain 1.03 g of a white mass of tetraacetyldibenzylhexaazaisowurtzitane (yield: 75%). From the below-mentioned results of the analysis by FD-mass spectrometry, $^1$H-NMR, $^{13}$C-NMR and $^{13}$C-$^1$H COSY, it was confirmed that the white mass obtained by the recrystallization was tetraacetyldibenzylhexaazaisowurtzitane. The results of the above-mentioned analysis are as follows.

FD-mass spectrum: 517 ([M+H]$^+$). $^1$H-NMR spectrum [solvent: CDCl$_3$; standard: TMS; unit: δ (ppm)]: 1.94 (s, 6H, COCH$_3$), 2.15 (s, 6H, COCH$_3$), 4.06 (d, 2H, CH$_2$), 4.29 (d, 2H, CH$_2$), 5.09 (d, 2H, CH), 5.70 (d, 2H, CH), 6.42 (S, 2H, CH) and 7.3–7.5 (m, 10H, Ph).

By $^1$H-NMR, 6 methine groups of the W skeleton, 4 acetyl groups and 2 benzyl groups could be identified. $^{13}$C-NMR [solvent: CDCl$_3$; standard: TMS; unit: δ (ppm)]: 20.737 (CH$_3$), 22.111 (CH$_3$), 56.428 (CH$_2$), 69.679 (CH), 70.592 (CH), 128.056 (Ph), 128.673 (Ph), 128.928 (Ph), 136.742) (Ph) and 168.263 (CO).

By $^{13}$C-NMR, methine groups of the W skeleton, acetyl groups, and phenyl groups and methylene groups of benzyl groups could be identified.

By $^1$H-$^3$C COSY, $^{13}$C's bonded to respective $^1$H's identified by the above $^1$H-NMR could be identified.

Example 20

Synthesis of WA$_4$(NO$_2$)$_2$ by Nitrosating WA$_4$H$_2$ to Prepare WA$_4$(NO)$_2$, and Oxidizing the WA$_4$(NO)$_2$ 0.336 g (1 mmol) of tetraacetylhexaazaisowurtzitane and 10 ml of 50% acetic acid as a solvent were charged into a 100 ml reaction vessel. The resultant mixture was cooled to and maintained at 0° C. While stirring the mixture at 0° C., 2 ml of an aqueous solution of sodium nitrite (concentration of sodium nitrite: 4 mol/l) was gradually added dropwise to the mixture. Subsequently, the resultant mixture was heated to 30° C., and then stirred for 4 hours to perform a nitrosation reaction. To the resultant reaction mixture was added 50 ml of chloroform. The resultant mixture was vigorously stirred, and then allowed to stand, so that the mixture separated into an organic phase and an inorganic phase. The organic phase was isolated and the solvent was distilled off under reduced pressure from the organic phase, to thereby obtain 0.373 g of dinitrosotetraacetylhexaazaisowurtzitane (yield: 95%). 30 ml of 100% nitric acid (an oxidizing agent) was charged to a 100 ml reaction vessel. Then, 0.9262 g (2.35 mmol) of the above-mentioned dinitrosotetraacetylhexaazaisowurtzitane was added to the reaction vessel. The resultant mixture was stirred at room temperature for 5 hours to perform a nitration reaction. Subsequently, the resultant reaction mixture was subjected to distillation under reduced pressure to distill off the nitric acid, thereby obtaining 0.955 g of dinitrotetraacetylhexaazaisowurtzitane (yield: 95%).

Results of the analysis of the obtained dinitrosotetraacetylhexaazaisowurtzitane are as follows.

Results of $^1$H-NMR [solvent: CDCl$_3$; standard: TMS; unit: δ (ppm)]: 2.05 (s, 6H, COCH$_3$), 2.17 (s, 6H, COCH$_3$), 5.46 (m, 2H, CH), 6.62 (m, 2H, CH) and 7.30 (s, 2H, CH).

By $^1$H-NMR, 6 methine groups of the W and 4 acetyl groups could be identified.

Results of infrared absorption spectrometry (IR) showed an absorption around 1,670 cm$^{-1}$, wherein the absorption is ascribed to a carbonyl group (C=O) of the acetyl group, and also showed absorptions around 1,500 cm$^{-1}$, 1,380 cm$^{-1}$ and 1,350 cm$^{-1}$, wherein each absorption is ascribed to a nitroso group.

Results of IR showed that the absorption ascribed to the N—H group, which was identified in the IR spectrum of tetraacetylhexaazaisowurtzitane, completely disappeared.

Next, results of the analysis of the dinitrotetraacetylhexaazaisowurtzitane are as follows.

Results of $^1$H-NMR [solvent: DMSO-d$_6$, standard: TMS; unit: δ (ppm)]: 2.10 (s, 12H, COCH$_3$), 6.75 (m, 2H, CH) and 7.35 (this peak has a singlet peak top at 7.35 ppm and a shoulder on the low magnetic field side of the singlet peak top, 4H, CH).

The results of infrared absorption spectrum showed an absorption around 1,680 cm$^{-1}$, wherein the absorption is ascribed to the stretching vibration of a carbonyl group (C=O) of the acetyl group, and also showed absorptions around 1,570 cm$^{-1}$ and 1,300 cm$^{-1}$, wherein each of the absorptions is ascribed to the stretching vibration of a nitro group. This indicates that a nitro group and an acetyl group are present as substituents on the W skeleton of the dinitrotetraacetylhexaazaisowurtzitane.

By FD-mass spectrometry, a parent ion peak (m/z426) could be identified.

The decomposition temperature of the dinitrotetraacetylhexaazaisowurtzitane was measured by differential scanning calorimetry (DSC) (a rate of temperature elevation: 10° C./min) using DSC 220C manufactured and sold by Seiko Instruments Inc., Japan. As a result, it was found that the peak temperature was about 314° C., which is higher than the peak temperature (about 250° C.) of HNW. This indicates that the dinitrotetraacetylhexaazaisowurtzitane is a nitramine compound having excellent heat resistance.

Example 21

Synthesis of WA$_4$(NO$_2$)$_2$ by Nitrating WA$_6$ 5 ml of acetic anhydride is charged into a 100 ml reaction vessel, and cooled to and maintained at 0° C. While stirring the acetic anhydride at 0° C., 5 ml of 100% nitric acid (nitrating agent) was gradually added dropwise to the reaction vessel. To the resultant mixture was added 0.5 g of dinitrogen pentaoxide (nitrating agent). Subsequently, to the resultant mixture was added 0.1 g (0.238 mmol) of hexaacetylhexaazaisowurtzitane. Then, to the resultant mixture was added 0.5 g of dinitrogen pentaoxide. This operation of addition of 0.5 g of dinitrogen pentaoxide was repeated 4 times at intervals of 1 hour. The resultant mixture was quenched with water and ice. The liquid components of the mixture were distilled off under reduced pressure, and the resultant solid residue was analyzed by high performance liquid chromatography. As a result, it was confirmed that the solid residue was dinitrotetraacetylhexaazaisowurtzitane.

Example 22

Synthesis of $W(NO_2)_6$ by Nitration of $WA_4(NO_2)_2$

A 200 ml reaction vessel was immersed in a 0° C. bath. 25 ml of sulfuric acid was charged into the reaction vessel, and then 25 ml of 100% nitric acid was gradually dropwise added to the reaction vessel to obtain a mixed acid (nitrating agent). To the obtained mixed acid was added 0.2 g (0.457 mmol) of dinitrotetraacetylhexaazaisowurtzitane, and the resultant mixture was stirred at 0° C. for 8 hours. Then, the mixture was further stirred at room temperature for 67 hours to perform a reaction thereof. After completion of the reaction, 200 ml of chloroform was added to the resultant reaction mixture, to thereby extract organic substances in the reaction mixture into a chloroform phase (this extraction operation was repeated twice). The chloroform phase was subjected to distillation under reduced pressure to distill off the solvent. The resultant solid residue was washed with an aqueous 10% solution of $NaHCO_3$, to thereby obtain 0.06 g of hexanitrohexaazaisowurtzitane (yield: 30%). Results of the analysis of the obtained hexanitrohexaazaisowurtzitane are as follows.

The results of infrared absorption spectroscopy by KBr method showed the following absorptions: an absorption around 1605 $cm^{-1}$ which is ascribed to the antisymmetric stretching vibration of a nitro group; absorptions around 1325 $cm^{-1}$ and around 1270 $cm^{-1}$, each of which absorptions is ascribed to the symmetric stretching vibration of a nitro group; absorptions around 945 $cm^{-1}$ and around 880 $cm^{-1}$, each of which absorptions is ascribed to the bending vibration of a nitro group; and an absorption around 3030 $cm^{-1}$ which is ascribed to the stretching vibration of a methine group on the W skeleton.

These infrared absorption characteristics are in agreement with the infrared absorption characteristics of hexanitrohexaazaisowurtzitane which are disclosed in COMBUSTION AND FLAME 87: 145–151 (1991). The above results of infrared absorption spectrometry also showed that an absorption around 1680 $cm^{-1}$ which is ascribed to a carbonyl group (C=O) of the acetyl group of dinitrotetraacetylhexaazaisowurtzitane (which was used as a starting material) completely disappeared.

The above results show that the acetyl groups of dinitrotetraacetylhexaazaisowurtzitane were replaced with nitro groups to form hexanitrohexaazaisowurtzitane.

The results of the analysis of the obtained hexanitrohexaazaisowurtzitane (HNW) by high performance liquid chromatography which was conducted under the same conditions as in International Symposium on Energetic Materials Technology PROCEEDINGS, SEPTEMBER 24–27, 76–81 (1995) (in which various characteristics of HNW are reported) showed that the obtained HNW had the same retention time as that of HNW disclosed in this publication.

The results of EI-mass spectroscopy showed the presence of fragment peaks, such as ion peaks 392 [molecular weight of HNW (parent ion) minus molecular weight of $NO_2$], 316, 213 and 46 ($NO_2$), wherein the ion peaks are in agreement with the ion peaks of the HNW which are disclosed in the above-mentioned International Symposium on Energetic Materials Technology PROCEEDINGS, SEPTEMBER 24–27, 76–81 (1995).

Comparative Example 1

Acylation Reaction After the Reductive Dearylmethylation of $WB_6$ in the Absence of an Acylating Agent 3.0 g (4.24 mmol) of hexabenzylhexaazaisowurtzitane, 0.476 g (2.12 mmol) of $Pd(OAc)_2$, 75 ml of tetrahydrofuran (THF) and 75 ml of ethanol were charged, together with a stirring element, into a 300 ml microbomb. The bomb was purged with hydrogen gas. Then, hydrogen gas was introduced into the bomb so that the internal pressure of the bomb became 10 $kgf/cm^2$-G. Then, the contents of the bomb were stirred at room temperature for 300 hours to perform a reaction thereof. After completion of the reaction, the amount of toluene formed by dearylmethylation of $WB_6$ was measured by gas chromatography. As a result, it was found that almost 100% of the benzyl groups had been removed. Then, the reaction mixture was taken out from the bomb, and the reduction catalyst was removed from the reaction mixture. Then, the solvent was distilled off under reduced pressure from the mixture. To the resultant residue was added 100 ml of acetic anhydride as an acetylating agent, followed by addition thereto of 10 ml of acetic chloride. However, the results of gas chromatography showed that a hexaazaisowurtzitane derivative having an acyl group was not formed.

From the above results, it was found that when the reductive dearylmethylation of $WB_6$ was conducted in the absence of an acylating agent, the decomposition of the W structure occurred.

Comparative Example 2

Acylation Reaction Conducted After the Reductive Dearylmethylation of $WB_6$ in the Absence of an Acylating Agent The reductive dearylmethylation of hexabenzylhexaazaisowurtzitane in the absence of an acylating agent was conducted in substantially the same manner as in Example 19, except that the acylating agent was not used. After completion of the reaction, the same amount of the same acylating agent as in Example 19 was added to the reaction mixture. The mixture was stirred under nitrogen atmosphere for 5 hours to perform a reaction thereof. The resultant reaction mixture was treated in the same manner as in Example 19. However, the presence of tetraacetyldibenzylhexaazaisowurtzitane could not be identified in the reaction mixture.

INDUSTRIAL APPLICABILITY

According to the present invention, an acyl group-containing hexaazaisowurtzitane derivative can be obtained. The acyl group-containing hexaazaisowurtzitane derivative is useful as a precursor of a polynitrohexaazaisowurtzitane derivative which can be used not only as a material for explosives but also as an additive for propellants and explosives. The acyl group-containing hexaazaisowurtzitane derivative of the present invention is also useful as a raw material for producing a highly polar polymer, and as a polyfunctional crosslinking agent and an additive for polymers.

What is claimed is:

1. An acyl group-containing hexaazaisowurtzitane compound represented by the following formula (I):

$$WA_tQ_{(6-t)} \quad (I)$$

wherein:

each A independently represents an acyl group selected from the group consisting of an acetyl group, a propionyl group, a butyryl group, an isobutyryl group, a valeryl group, a hexanoyl group and a 2-phenylacetyl group, each Q independently represents a hydrogen atom or an alkyl group having 1 to 10 carbon atoms, t represents an integer of from 4 to 5, with the proviso that t is 5 when Q is a hydrogen atom and that t is 4 or 5 when Q is an alkyl group having 1 to 10 carbon atoms, and W represents a hexavalent hexaazaisowurtzitane residue represented by the following formula (II):

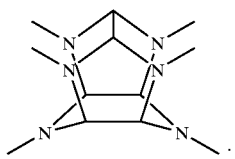

(II)

2. The acyl group-containing hexaazaisowurtzitane compound according to claim 1 which is represented by the following formula:

$$WA_5H$$

wherein each of A and W is as defined for formula (I) in claim 1 and H is a hydrogen atom.

3. An acyl group-containing hexaazaisowurtzitane compound, which is in the form of a mixture of $$WA_5H,$$

$$WA_4H_2,$$

and $$WA_6$$

wherein each H is a hydrogen atom, wherein each A independently represents an acyl group selected from the group consisting of an acetyl group, a propionyl group, a butyryl group, an isobutyryl group, a valeryl group, a hexanoyl group and a 2-phenylacetyl group, and wherein each W represents a hexavalent hexaazaisowurtzitane residue represented by the following formula (II):

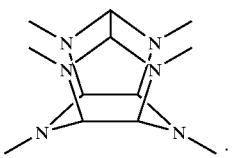

(II)

4. A method for producing a hexaacylhexaazaisowurtzitane represented by the following formula (III):

$$WA_6 \quad (III)$$

wherein each A independently represents an acyl group selected from the group consisting of an acetyl group, a propionyl group, a butyryl group, an isobutyryl group, a valery group, a hexanoyl group and a 2-phenylacetyl group, and W represents a hexavalent hexaazaisowurtzitane residue represented by the following formula (II):

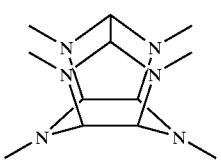

(II)

W which comprises acylating a hexaazaisowurtzitane compound represented by the following formula:

$$WA_5H$$

wherein H represents a hydrogen atom, and each of A and W is as defined above for formula (III)

with an acylating agent.

5. The method according to claim 4, wherein said hexaazaisowurtzitane compound represented by the formula:

$$WA_5H$$

wherein H represents a hydrogen atom, each A independently represents an acyl group selected from the group consisting of an acetyl group, a propionyl group, a butyryl group, an isobutyryl group, a valeryl group, a hexanoyl group and a 2-phenylacetyl group, and W represents a hexavalent hexaazaisowurtzitane residue represented by the following formula (II):

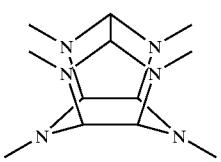

(II)

is produced by subjecting an acyl group- and arylmethyl group-containing hexaazaisowurtzitane compound represented by the following formula:

$$WA_5B$$

wherein B represents an arylmethyl group having 7 to 21 carbon atoms, and each of A and W is as defined above to reductive dearylmethylation in the absence of an acylating agent.

6. The method according to claim 5, wherein said acyl group- and arylmethyl group-containing hexaazaisowurtzitane compound represented by the following formula:

$$WA_5B$$

wherein each A independently represents an acyl group selected from the group consisting of an acetyl group, a propionyl group, a butyryl group, an isobutyryl group, a valeryl group, a hexanoyl group and a 2-phenylacetyl group, and W represents a hexavalent hexaazaisowurtzitane residue represented by the following formula (II):

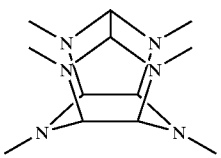
(II)

is produced by subjecting a hexakis(arylmethyl) hexaazaisowurtzitane represented by the following formula (XI):

$$WB_6 \qquad (XI)$$

wherein W is as defined above, and wherein each B independently represents an arylmethyl group having 7 to 21 carbon atoms to reductive dearylmethylation in the presence of an acylating agent.

7. The method according to claim 6, wherein said acylating agent is a carboxylic ester of N-hydroxysuccinimide, a mixture of a carboxylic anhydride and a carboxylic ester of N-hydroxysuccinimide, or a carboxylic anhydride.

8. The method according to claim 4, wherein said acylating agent is an acyl halide.

* * * * *

UNITED STATES PATENT AND TRADEMARK OFFICE
CERTIFICATE OF CORRECTION

PATENT NO.     : 6,472,525 B1
DATED          : October 29, 2002
INVENTOR(S)    : Tamotsu Kodama et al.

It is certified that error appears in the above-identified patent and that said Letters Patent is hereby corrected as shown below:

<u>Column 38,</u>
Line 20, "valery" should read -- valeryl --.
Line 34, before "which" delete "W".

Signed and Sealed this

Thirteenth Day of May, 2003

JAMES E. ROGAN
*Director of the United States Patent and Trademark Office*